United States Patent
Maruoka

(10) Patent No.: US 6,441,231 B1
(45) Date of Patent: Aug. 27, 2002

(54) OPTICALLY ACTIVE QUARTERNARY AMMONIUM SALT WITH AXIAL CHIRALITY, METHOD FOR PRODUCING THEREOF, AND APPLICATION THEREOF FOR ASYMMETRIC SYNTHESIS OF α-AMINO ACID

(75) Inventor: Keiji Maruoka, Ohtsu (JP)

(73) Assignee: Nagase & Co., Ltd., Osaka (JP)

( * ) Notice: Subject to any disclaimer, the term of this patent is extended or adjusted under 35 U.S.C. 154(b) by 0 days.

(21) Appl. No.: 09/987,544

(22) Filed: Nov. 15, 2001

Related U.S. Application Data

(62) Division of application No. 09/616,361, filed on Jul. 13, 2000, now Pat. No. 6,340,753.

(51) Int. Cl.$^7$ ............................................. C07C 229/06

(52) U.S. Cl. ......................... 564/35; 564/125; 564/168

(58) Field of Search ........................... 564/35, 125, 168

(56) References Cited

PUBLICATIONS

Takashi Ooi, et al., "Molecular Design of a $C_2$–Symmetric Chiral Phase–Transfer Catalyst for Practical Asymmetric Synthesis of α–Amino Acids", J.Am.Chem.Soc., vol. 121, No. 27, 1999 pp. 6519–6520.

Takashi Ooi, et al., "Practical Catalytic Enantioselective Synthesis of a α–Dialkyl α–Amino Acids by Chiral Phase–Transfer Catalysis", J.Am. Chem. Soc., vol. 122, No. 21, 2000 pp. 5228–5229 w. 2000 American Chemical Society, J.Am.Chem.Socl, Ooi ja0007051 Supporting Info pp. 1–3.

*Primary Examiner*—Bruck Kifle
(74) *Attorney, Agent, or Firm*—Oblon, Spivak, McClelland, Maier & Neustadt, P.C.

(57) ABSTRACT

A novel optically active quarternary ammonium salt with an axial chirality is provided. The quarternary ammonium salt can act as a phase-transfer catalyst to convert glycine derivatives into optically active α-amino acid derivatives by stereoselectively alkylating the glycine derivatives. Furthermore, according to the present invention, intermediates useful for producing the novel quarternary ammonium can be produced.

4 Claims, No Drawings

OPTICALLY ACTIVE QUARTERNARY AMMONIUM SALT WITH AXIAL CHIRALITY, METHOD FOR PRODUCING THEREOF, AND APPLICATION THEREOF FOR ASYMMETRIC SYNTHESIS OF α-AMINO ACID

This application is a division of application Ser. No. 09/616,361 filed on Jul. 13, 2000 now U.S. Pat. No. 6,340,753.

BACKGROUND OF THE INVENTION

1. Field of the Invention

The present invention relates to a novel optically active quarternary ammonium salt having $C_2$-symmetric axial chirality, a method for producing thereof, and an intermediate for producing the salt and a method for producing the intermediate. Further, the present invention relates to a method for producing optically active α-amino acid derivatives by stereoselective alkylation using the salts as a phase-transfer catalyst.

2. Description of the Related Art

A method is reported that cincona alkaloid derivatives are used as a phase-transfer catalyst for producing optically active α-amino acid derivatives expressed by a general formula (XXI):

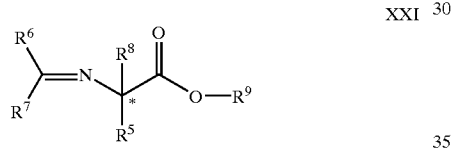

XXI wherein $R^5$ is an alkyl group having 1 to 6 carbon atoms which may be branched or form a cyclic group; an allyl or substituted allyl group having 3 to 9 carbon atoms which may be branched or form a cyclic group; an aralkyl group which may be substituted with an alkyl group having 1 to 4 carbon atoms, an alkoxy group having 1 to 3 carbon atoms, a halogen atom, an aryl group which may be substituted with an alkyl group having 1 to 4 carbon atoms, an alkoxy group having 1 to 3 carbon atoms or a halogen atom, or a heteroaryl group which may be substituted with an alkyl group having 1 to 4 carbon atoms, an alkoxy group having 1 to 3 carbon atoms or a halogen atom; a heteroaralkyl group which may be substituted with an alkyl group having 1 to 4 carbon atoms, an alkoxy group having 1 to 3 carbon atoms, a halogen atom, an aryl group which may be substituted with an alkyl group having 1 to 4 carbon atoms, an alkoxy group having 1 to 3 carbon atoms or a halogen atom, or a heteroaryl group which may be substituted with an alkyl group having 1 to 4 carbon atoms, an alkoxy group having 1 to 3 carbon atoms or a halogen atom; or a propargyl or substituted propargyl group which having 3 to 9 carbon atoms which may be branched; and

* is a newly produced chiral center (Corey, E. J. et al. J. Am. Chem. Soc., 1997, 119, 12414).

The above-mentioned compound of general formula (XXI) are produced by stereoselectively alkylating a glycine derivative expressed by a general formula (XIX):

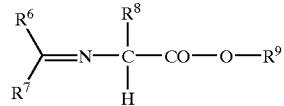

XIX in the two phase system comprised or organic solvent and water, with a compound of general formula (XX):

$$R^5-W \qquad (XX)$$

wherein $R^5$ is an alkyl group having 1 to 6 carbon atoms which may be branched or form a cyclic group; an allyl or substituted allyl group having 3 to 9 carbon atoms which may be branched or form a cyclic group; an aralkyl group which may be substituted with an alkyl group having 1 to 3 carbon atoms, an alkoxy group having 1 to 3 carbon atoms, a halogen atom, an aryl group which may be substituted with an alkyl group having 1 to 4 carbon atoms, an alkoxy group having 1 to 3 carbon atoms or a halogen atom, or a heteroaryl group which may be substituted with an alkyl group having 1 to 4 carbon atoms, an alkoxy group having 1 to 3 carbon atoms or a halogen atom; a heteroaralkyl group which may be substituted with an alkyl group having 1 to 4 carbon atoms, an alkoxy group having 1 to 3 carbon atoms, a halogen atom, an aryl group which may be substituted with an alkyl group having 1 to 4 carbon atoms, an alkoxy group having 1 to 3 carbon atoms or a halogen atom, or a heteroaryl group which may be substituted with an alkyl group having 1 to 4 carbon atoms, an alkoxy group having 1 to 3 carbon atoms or a halogen atom; or a propargyl or substituted propargyl group which having 3 to 9 carbon atoms which may be branched; and W is a functional group having leaving ability.

However, in the above-mentioned conventional method, halogenized solvent should be used as a solvent and since reaction temperature should be very low for producing the chiral derivatives with high purity, above-mentioned method is not used for industrial production.

Furthermore, since the phase-transfer catalyst is prepared from cincona alkaloid, it is difficult to modify or prepare derivatives of a catalyst having an excellent stereoselectivity based on the above-mentioned phase-transfer catalyst.

On the other hand, it is not known that optically active quarternary ammonium salt with axial chirality is prepared and used for stereoselective alkylation as a phase-transfer catalyst.

SUMMARY OF THE INVENTION

The purpose of the present invention is to provide an optically active quarternary ammonium salt with axial chirality, particularly their spiro derivatives, as a phase-transfer catalyst. The quarternary ammonium salt of the present invention converts glycine derivatives into optically active α-amino acid derivatives by stereoselectively alkylating the glycine derivatives. Moreover, the purpose of the present invention is to provide an intermediates useful for production of the novel quarternary ammonium salt.

The present invention provides a compound of general formula (I):

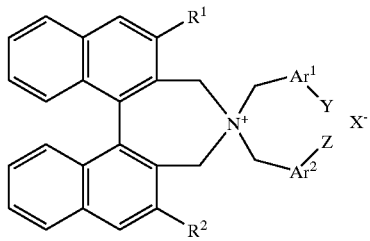

wherein $R^1$ and $R^2$ are groups independently selected from the group consisting of a hydrogen atom; an alkyl group having 1 to 6 carbon atoms which may be branched or form a cyclic group; an alkenyl group having 2 to 6 carbon atoms which may be branched or form a cyclic group; an alkynyl group having 2 to 6 carbon atoms which may contain branched or cyclic structure; an aralkyl group which may be substituted with an alkyl group having 1 to 4 carbon atoms, an alkoxy group having 1 to 3 carbon atoms or a halogen atom; a heteroaralkyl group which may be substituted with an alkyl group having 1 to 4 carbon atoms, an alkoxy group having 1 to 3 carbon atoms or a halogen atom; an aryl group which may be substituted with an alkyl group having 1 to 4 carbon atoms, an alkoxy group having 1 to 3 carbon atoms or a halogen atom; a heteroaryl group which may be substituted with an alkyl group having 1 to 4 carbon atoms, an alkoxy group having 1 to 3 carbon atoms or a halogen atom; a ($C_1$ to $C_3$ alkoxy) carbonyl group; a carbamoyl group; a N-($C_1$ to $C_4$ alkyl) carbamoyl group; and a N,N-di($C_1$ to $C_4$ alkyl) carbamoyl group (wherein alkyl may be the same or different), and $R^1$ and $R^2$ may be the same or different;

$Ar^1$ and $Ar^2$ are groups independently selected from the group consisting of an aryl group which may be substituted with an alkyl group having 1 to 4 carbon atoms, an alkoxy group having 1 to 3 carbon atoms or a halogen atom; and a heteroaryl group which may be substituted with an alkyl group having 1 to 4 carbon atoms, an alkoxy group having 1 to 3 carbon atoms or a halogen atom, and $Ar^1$ and $Ar^2$ may be the same or different;

$X^-$ is a halide anion; and

Y and Z are groups independently selected from the group consisting of a hydrogen atom; a halogen atom; an alkyl group having 1 to 4 carbon atoms; and an alkoxy group having 1 to 3 carbon atoms, and Y and Z may be the same or different or may form a single bond. Thus, the above purpose are achieved.

In a preferred embodiment of the present invention, the above compound is a spiro type and Y and Z form a single bond, and the compound is expressed by a general formula (II):

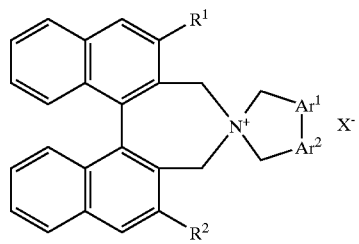

In a preferred embodiment of the present invention, $Ar^1$ and $Ar^2$ are β-naphthyl groups, each $Ar^1$ and $Ar^2$ is bound to α-site of the other group, $X^-$ is a bromide anion, and the compound is expressed by a general formula (III):

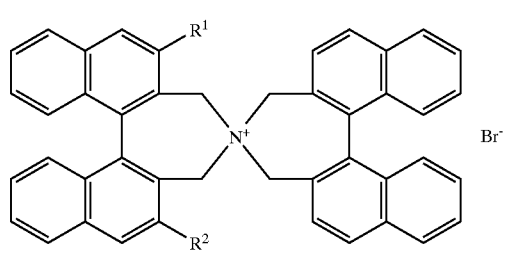

In a preferred embodiment of the present invention, both $R^1$ and $R^2$ are phenyl, or both $R^1$ and $R^2$ are β-naphthyl.

Moreover, the present invention provides a method for producing the compound of the general formula (I), comprising reacting a compound of general formula (IV):

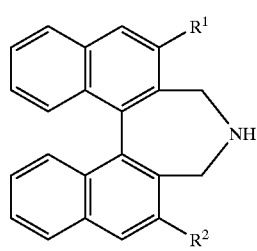

wherein $R^1$ and $R^2$ are groups independently selected from the group consisting of a hydrogen atom; an alkyl group having 1 to 6 carbon atoms which may be branched or form a cyclic group; an alkenyl group having 2 to 6 carbon atoms which may be branched or form a cyclic group; an alkynyl group having 2 to 6 carbon atoms which may contain branched or cyclic structure; an aralkyl group which may be substituted with an alkyl group having 1 to 4 carbon atoms, an alkoxy group having 1 to 3 carbon atoms or a halogen atom; a heteroaralkyl group which may be substituted with an alkyl group having 1 to 4 carbon atoms, an alkoxy group having 1 to 3 carbon atoms or a halogen atom; an aryl group which may be substituted with an alkyl group having 1 to 4 carbon atoms, an alkoxy group having 1 to 3 carbon atoms or a halogen atom; a heteroaryl group which may be substituted with an alkyl group having 1 to 4 carbon atoms, an alkoxy group having 1 to 3 carbon atoms or a halogen atom; a ($C_1$ to $C_3$ alkoxy) carbonyl group; a carbamoyl group;

a N-($C_1$ to $C_4$ alkyl) carbamoyl group; and a N,N-di($C_1$ to $C_4$ alkyl) carbamoyl group (wherein alkyl may be the same or different), and $R^1$ and $R^2$ may be the same or different;

with a compound of general formula (V):

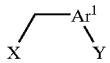

V and a compound of general formula (VI):

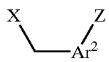

VI wherein, in the general formulae (V) and (VI), $Ar^1$ and $Ar^2$ are groups independently selected from the group consisting of an aryl group which may be substituted with an alkyl group having 1 to 4 carbon atoms, an alkoxy group having 1 to 3 carbon atoms or a halogen atom; and a heteroaryl group which may be substituted with an alkyl group having 1 to 4 carbon atoms, an alkoxy group having 1 to 3 carbon atoms or a halogen atom;

$Ar^1$ and $Ar^2$ may be the same or different;

X is a halogen atom; and

Y and Z are groups independently selected from the group consisting of a hydrogen atom; a halogen atom; an alkyl group having 1 to 4 carbon atoms; and an alkoxy group having 1 to 3 carbon atoms, and Y and Z may be the same or different or may form a single bond; in this order or simultaneously, in the presence of an acid capturing agent and in an appropriate solvent.

Moreover, the present invention provides a method for producing the compound of the general formula (II), comprising reacting a compound of general formula (IV):

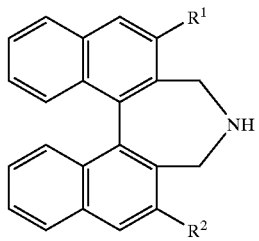

IV wherein $R^1$ and $R^2$ are groups independently selected from the group consisting of a hydrogen atom; an alkyl group having 1 to 6 carbon atoms which may be branched or form a cyclic group; an alkenyl group having 2 to 6 carbon atoms which may be branched or form a cyclic group; an alkynyl group having 2 to 6 carbon atoms which may contain branched or cyclic structure; an aralkyl group which may be substituted with an alkyl group having 1 to 4 carbon atoms, an alkoxy group having 1 to 3 carbon atoms or a halogen atom; a heteroaralkyl group which may be substituted with an alkyl group having 1 to 4 carbon atoms, an alkoxy group having 1 to 3 carbon atoms or a halogen atom; an aryl group which may be substituted with an alkyl group having 1 to 4 carbon atoms, an alkoxy group having 1 to 3 carbon atoms or a halogen atom; a heteroaryl group which may be substituted with an alkyl group having 1 to 4 carbon atoms, an alkoxy group having 1 to 3 carbon atoms or a halogen atom; a ($C_1$ to $C_3$ alkoxy) carbonyl group; a carbamoyl group; a N-($C_1$ to $C_4$ alkyl) carbamoyl group; and a N,N-di($C_1$ to $C_4$ alkyl) carbamoyl group (wherein alkyl may be the same or different); and $R^1$ and $R^2$ may be the same or different;

with a compound of general formula (VII):

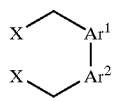

VII wherein $Ar^1$ and $Ar^2$ are groups independently selected from the group consisting of an aryl group which may be substituted with an alkyl group having 1 to 4 carbon atoms, an alkoxy group having 1 to 3 carbon atoms or a halogen atom; and a heteroaryl group which may be substituted with an alkyl group having 1 to 4 carbon atoms, an alkoxy group having 1 to 3 carbon atoms or a halogen atom, and $Ar^1$ and $Ar^2$ may be the same or different; X is a halogen atom;

in the presence of an acid capturing agent and in an appropriate solvent.

Moreover, the present invention provides a compound of general formula (VIII):

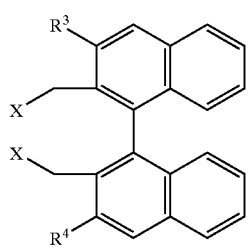

VII wherein $R^3$ and $R^4$ are groups independently selected from the group consisting of a hydrogen atom; an alkyl group having 1 to 6 carbon atoms which may be branched or form a cyclic group; an alkenyl group having 2 to 6 carbon atoms which may be branched or form a cyclic group; an alkynyl group having 2 to 6 carbon atoms which may contain branched or cyclic structure; an aralkyl group which may be substituted with an alkyl group having 1 to 4 carbon atoms, an alkoxy group having 1 to 3 carbon atoms or a halogen atom; a heteroaralkyl group which may be substituted with an alkyl group having 1 to 4 carbon atoms, an alkoxy group having 1 to 3 carbon atoms or a halogen atom; an aryl group which may be substituted with an alkyl group having 1 to 4 carbon atoms, an alkoxy group having 1 to 3 carbon atoms or a halogen atom; a heteroaryl group which may be substituted with an alkyl group having 1 to 4 carbon atoms, an alkoxy group having 1 to 3 carbon atoms or a halogen atom; ($C_1$ to $C_3$ alkoxy) carbonyl group; a carbamoyl group; a N-($C_1$ to $C_4$ alkyl) carbamoyl group; and a N,N-di($C_1$ to $C_4$ alkyl) carbamoyl group (wherein alkyl may be the same or different), and R³ and R⁴ may be the same or different; and X is a halogen atom.

In a preferred embodiment of the present invention, both R³ and R⁴ are phenyl, or both R³ and R⁴ are β-naphthyl, and X is a bromine atom.

Moreover, the present invention provides a method for producing a compound of general formula (III), comprising reacting optically active 3,5-dihydro-4H-dinaphtho[2,3-c:1', 2'-e]azepine expressed by a formula (IX):

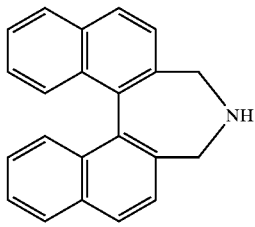

IX with a compound of a general formula (X):

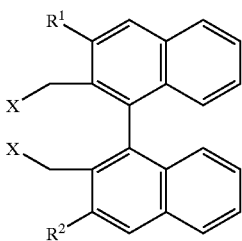

X wherein

R¹ and R² are groups independently selected from the group consisting of a hydrogen atom; an alkyl group having 1 to 6 carbon atoms which may be branched or form a cyclic group; an alkenyl group having 2 to 6 carbon atoms which may be branched or form a cyclic group; an alkynyl group having 2 to 6 carbon atoms which may contain branched or cyclic structure; an aralkyl group which may be substituted with an alkyl group having 1 to 4 carbon atoms, an alkoxy group having 1 to 3 carbon atoms or a halogen atom; a heteroaralkyl group which may be substituted with an alkyl group having 1 to 4 carbon atoms, an alkoxy group having 1 to 3 carbon atoms or a halogen atom; an aryl group which may be substituted with an alkyl group having 1 to 4 carbon atoms, an alkoxy group having 1 to 3 carbon atoms or a halogen atom; a heteroaryl group which may be substituted with an alkyl group having 1 to 4 carbon atoms, an alkoxy group having 1 to 3 carbon atoms or a halogen atom; a ($C_1$ to $C_3$ alkoxy) carbonyl group; a carbamoyl group; a N-($C_1$ to $C_4$ alkyl) carbamoyl group; and a N,N-di($C_1$ to $C_4$ alkyl) carbamoyl group (wherein alkyl may be the same or different), and R¹ and R² may be the same or different; and;

X is a halogen atom;

in an alcoholic solvent and in a presence of inorganic base as an acid capturing agent.

Moreover, the present invention provides a method for producing the compound of Claim 4, comprising reacting a compound of a formula (IX):

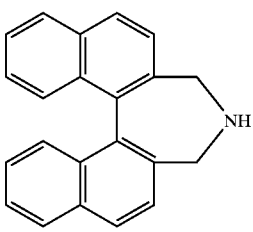

IX with the compound of Claim 8 in alcohol solvent and in the presence of inorganic base as an acid capturing agent.

Moreover, the present invention provides a compound of a general formula (XI):

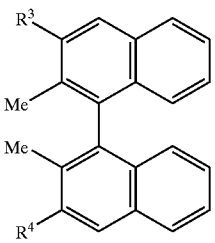

XI wherein

R³ and R⁴ are groups independently selected from the group consisting of a hydrogen atom; an alkyl group having 1 to 6 carbon atoms which may be branched or form a cyclic group; an alkenyl group having 2 to 6 carbon atoms which may be branched or form a cyclic group; an alkynyl group having 2 to 6 carbon atoms which may contain branched or cyclic structure; an aralkyl group which may be substituted with an alkyl group having 1 to 4 carbon atoms, an alkoxy group having 1 to 3 carbon atoms or a halogen atom; a heteroaralkyl group which may be substituted with an alkyl group having 1 to 4 carbon atoms, an alkoxy group having 1 to 3 carbon atoms or a halogen atom; an aryl group which may be substituted with an alkyl group having 1 to 4 carbon atoms, an alkoxy group having 1 to 3 carbon atoms or a halogen atom; a heteroaryl group which may be substituted with an alkyl group having 1 to 4 carbon atoms, an alkoxy group having 1 to 3 carbon atoms or a halogen atom; a ($C_1$ to $C_3$ alkoxy) carbonyl group; a carbamoyl group; a N-($C_1$ to $C_4$ alkyl) carbamoyl group; and a N,N-di($C_1$ to $C_4$ alkyl) carbamoyl group (wherein alkyl may be the same or different), and R³ and R⁴ may be the same or different.

In a preferred embodiment of the present invention, both R³ and R⁴ are phenyl, or both R³ and R⁴ are β-naphthyl.

Further, the present invention provides a method for producing the compound of a general formula (VIII), comprising reacting the compound of Claim 11 with an appropriate halogenating agent which can generate a halogen radical in an appropriate solvent and in the presence of appropriate radical reaction initiator to halogenate both 2- and 2'-methyl groups.

Moreover, the present invention provides a method for producing the compound of Claim 8, comprising reacting the compound of Claim 12 with brominating agent which can generate a bromine radical in an appropriate solvent and in the presence of appropriate radical reaction initiator to brominate both 2- and 2'-methyl groups.

Moreover, the present invention provides a compound of a general formula (XII):

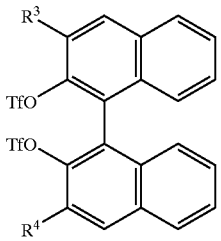

XII wherein $R^3$ and $R^4$ are groups independently selected from the group consisting of a hydrogen atom; an alkyl group having 1 to 6 carbon atoms which may be branched or form a cyclic group; an alkenyl group having 2 to 6 carbon atoms which may be branched or form a cyclic group; an alkynyl group having 2 to 6 carbon atoms which may contain branched or cyclic structure; an aralkyl group which may be substituted with an alkyl group having 1 to 4 carbon atoms, an alkoxy group having 1 to 3 carbon atoms or a halogen atom; an aryl group which may be substituted with an alkyl group having 1 to 4 carbon atoms, an alkoxy group having 1 to 3 carbon atoms or a halogen atom; a heteroaryl group which may be substituted with an alkyl group having 1 to 4 carbon atoms, an alkoxy group having 1 to 3 carbon atoms or a halogen atom; a ($C_1$ to $C_3$ alkoxy) carbonyl group; a carbamoyl group; a N-($C_1$ to $C_3$ alkyl) carbamoyl group; and a N,N-di($C_1$ to $C_3$ alkyl) carbamoyl group (wherein alkyl may be the same or different), and $R^3$ and $R^4$ may be the same or different; and Tf is a trifluoromethanesulfonyl group.

In a preferred embodiment of the present invention, both $R^3$ and $R^4$ are phenyl, or both $R^3$ and $R^4$ are β-naphthyl.

Moreover, the present invention provides a method for producing the compound of claim 11, comprising reacting the compound of Claim 15 with methylmagnesium halide expressed by a general formula (XIII):

<p align="center">MeMgX        (XIII)</p> wherein

X is a halogen atom, in the presence of nickel catalyst in an appropriate solvent.

Moreover, the present invention provides a method for producing the compound of Claim 12, comprising reacting the compound of Claim 16 with methylmagnesium halide expressed by a general formula (XIII):

<p align="center">MeMgX        (XIII)</p> wherein

X is a halogen atom, in the presence of nickel catalyst in an appropriate solvent.

Moreover, the present invention provides a compound of a formula (XIV):

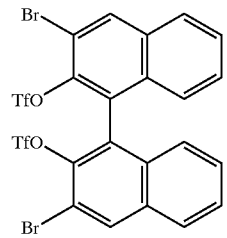

XIV wherein

Tf is a trifluoromethanesulfonyl group.

Moreover, the present invention provides a method for producing a compound of a general formula (XII'):

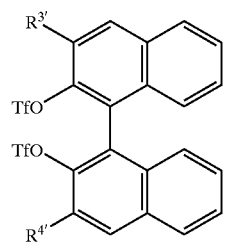

XII' wherein $R^{3'}$ and $R^{4'}$ are groups independently selected from the group consisting of an alkyl group having 1 to 6 carbon atoms which may be branched or form a cyclic group; an alkenyl group having 2 to 6 carbon atoms which may be branched or form a cyclic group; an alkynyl group having 2 to 6 carbon atoms which may contain branched or cyclic structure; an aralkyl group which may be substituted with an alkyl group having 1 to 4 carbon atoms, an alkoxy group having 1 to 3 carbon atoms or a halogen atom; an aryl group which may be substituted with an alkyl group having 1 to 4 carbon atoms, an alkoxy group having 1 to 3 carbon atoms or a halogen atom; a heteroaryl group which may be substituted with an alkyl group having 1 to 4 carbon atoms, an alkoxy group having 1 to 3 carbon atoms or a halogen atom; a ($C_1$ to $C_3$ alkoxy) carbonyl group; a carbamoyl group; a N-($C_1$ to $C_3$ alkyl) carbamoyl group; and a N,N-di($C_1$ to $C_3$ alkyl) carbamoyl group (wherein alkyl may be the same or different), and $R^{3'}$ and $R^{4'}$ may be the same or different; and Tf is a trifluoromethanesulfonyl group, comprising:

substituting a bromine atom in the compound of Claim 19 with $R^{3'}$ and $R^{4'}$ in an appropriate solvent and in the presence of transition metal catalyst.

Moreover, the present invention provides a method for producing the compound of a general formula (XVII):

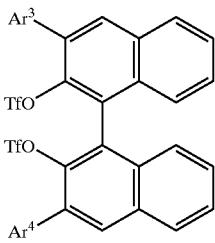

XVII wherein
Ar$^3$ and Ar$^4$ are groups selected from the groups consisting of an alkenyl group having 2 to 6 carbon atoms which may be branched or form a cyclic group; an aryl group which may be substituted with an alkyl group having 1 to 4 carbon atoms, an alkoxy group having 1 to 3 carbon atoms or a halogen atom; and a heteroaryl group which may be substituted with an alkyl group having 1 to 4 carbon atoms, an alkoxy group having 1 to 3 carbon atoms or a halogen atom, and Ar$^3$ and Ar$^4$ may be the same or different; comprising reacting the compound of Claim 19 with a compound of a general formula (XV):

Ar$^3$B(OH)$_2$  (XV)

and a compound of a general formula (XVI):

Ar$^4$B(OH)$_2$  (XVI)

wherein, in the general formulae (XV) and (XVI), Ar$^3$ and Ar$^4$ are groups selected from the group consisting of an alkenyl group having 2 to 6 carbon atoms which may be branched or form a cyclic group; an aryl group which may be substituted with an alkyl group having 1 to 4 carbon atoms, an alkoxy group having 1 to 3 carbon atoms or a halogen atom; and a heteroaryl group which may be substituted with an alkyl group having 1 to 4 carbon atoms, an alkoxy group having 1 to 3 carbon atoms, or a halogen atom, and Ar$^3$ and Ar$^4$ may be the same or different; in this order or simultaneously, in an appropriate solvent and in the presence of base and palladium catalyst.

Moreover, the present invention provides a method for producing the compound of Claim 16 comprising:

reacting the compound of Claim 19 with a compound of a general formula (XV):

Ar$^3$B(OH)$_2$  (XV)

and a compound of a general formula (XVI):

Ar$^4$B(OH)$_2$  (XVI)

wherein, in the general formulae (XV) and (XVI), both Ar$^3$ and Ar$^4$ are phenyl or β-naphthyl in an appropriate solvent and in the presence of base and palladium catalyst.

Moreover, the present invention provides a method for producing the compound of Claim 19 comprising:

reacting the compound for a formula (XVIII):

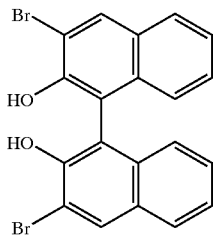

XVIII with a triflatating agent in an appropriate solvent and in the presence of base.

Further, the present invention provides a method of stereoselectively producing a compound of a general formula (XXI):

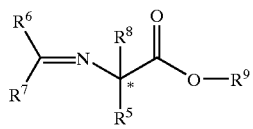

XXI wherein
R$^5$ is alkyl group having 1 to 6 carbon atoms which may be branched or form a cyclic group; an allyl or substituted allyl group having 3 to 9 carbon atoms which may be branched or form a cyclic group; an aralkyl group which may substituted with alkyl group having 1 to 4 carbon atoms, an alkoxy group having 1 to 3 carbon atoms, a halogen atom, an aryl group which may be substituted with an alkyl group having 1 to 4 carbon atoms, an alkoxy group having 1 to 3 carbon atoms or a halogen atom, or a heteroaryl group which may be substituted with an alkyl group having 1 to 4 carbon atoms, an alkoxy group having 1 to 3 carbon atoms or a halogen atom; a heteroaralkyl group which may be substituted with an alkyl group having 1 to 4 carbon atoms, an alkoxy group having 1 to 3 carbon atoms, a halogen atom, an aryl group which may be substituted with alkyl group having 1 to 4 carbon atoms, alkoxy group having 1 to 3 carbon atoms or a halogen atom, or heteroaryl group which may be substituted with an alkyl group having 1 to 4 carbon atoms, an alkoxy group having 1 to 3 carbon atoms or a halogen atom; or a propargyl or substituted propargyl group which has 3 to 9 carbon atoms which may be branched;

R$^6$ and R$^7$ are the same or different and may be a hydrogen atom, an aryl group which may be substituted with an alkyl group having 1 to 3 carbon atoms, an alkoxy group having 1 to 3 carbon atoms or a halogen atom, with the proviso that they are not both hydrogen atoms;

R$^8$ is a hydrogen atom; an aryl group which may be substituted with alkyl group having 1 to 3 carbon atoms, alkoxy group having 1 to 3 carbon atoms or a halogen atom; an alkyl group having 1 to 6 carbon atoms which may be branched or form a cyclic group; an aralkyl group which may be substituted with an alkyl group having 1 to 3 carbon atoms, or an alkoxy group having 1 to 3 carbon atoms or a halogen atom; and R$^9$ is an alkyl group having 1 to 4 carbon atoms;

comprising:
alkylating a compound expressed by a general formula (XIX):

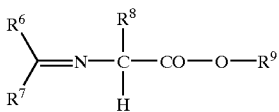

(XIX)

wherein $R^6$ and $R^7$ are the same or different and may be a hydrogen atom, an aryl group which may be substituted with an alkyl group having 1 to 3 carbon atoms, an alkoxy group having 1 to 3 carbon atoms or a halogen atom, with the proviso that they are not both hydrogen atoms; $R^8$ is a hydrogen atom; an aryl group which may be substituted with an alkyl group having 1 to 3 carbon atoms, an alkoxy group having 1 to 3 carbon atoms or a halogen atom; an alkyl group having 1 to 6 carbon atoms which may be branched or form a cyclic group; an aralkyl group which may be substituted with an alkyl group having 1 to 3 carbon atoms, an alkoxy group having 1 to 3 carbon atoms or a halogen atom; and $R^9$ is an alkyl group having 1 to 4 carbon atoms;

with a compound of a general formula (XX):

$$R^6\text{---}W \qquad\qquad (XX)$$

wherein $R^5$ is an alkyl group having 1 to 6 carbon atoms which may be branched or form a cyclic group; an allyl or substituted allyl group having 3 to 9 carbon atoms which may be branched or form a cyclic group; an aralkyl group which may be substituted with an alkyl group having 1 to 4 carbon atoms, an alkoxy group having 1 to 3 carbon atoms, a halogen atom, an aryl group which may be substituted with an alkyl group having 1 to 4 carbon atoms, an alkoxy group having 1 to 3 carbon atoms or a halogen atom, or a heteroaryl group which may be substituted with an alkyl group having 1 to 4 carbon atoms, an alkoxy group having 1 to 3 carbon atoms or a halogen atom; a heteroaralkyl group which may be substituted with an alkyl group having 1 to 3 carbon atoms, an alkoxy group having 1 to 3 carbon atoms, a halogen atom, an aryl group which may be substituted with an alkyl group having 1 to 3 carbon atoms, an alkoxy group having 1 to 3 carbon atoms or a halogen atom, or a heteroaryl group which may be substituted with an alkyl group having 1 to 4 carbon atoms, an alkoxy group having 1 to 3 carbon atoms or a halogen atom; or a propargyl or substituted propargyl group which has 3 to 9 carbon atoms which may be branched; and W is a functional group having leaving ability; using the compound of claim 1, which is pure regarding axial chirality, as a phase-transfer catalyst in an appropriate solvent and in the presence of an inorganic base.

In a preferred embodiment of the present invention, the phase-transfer catalyst is the compound of claim 2.

In a preferred embodiment of the present invention, the phase-transfer catalyst is the compound of claim 3.

In a preferred embodiment of the present invention, the phase-transfer catalyst is the compound of claim 4.

DESCRIPTION OF THE PREFERRED EMBODIMENT

The description and terms used herein are defined as follows:

The description "which may be bunched or form a cyclic group", used herein, means "which may be a linear chain, branched chain or ring structure".

The term "alkyl group(s) having 1 to 6 carbon atoms which may be branched or form a cyclic group" means any of linear, branched or cyclic alkyl group(s) having 1 to 6 carbon atoms, including a methyl, ethyl, n-propyl, isopropyl, cyclopropyl, n-butyl, sec-butyl, tert-butyl, cyclobutyl, pentyl, cyclopentyl, hexyl and cyclohexyl group. In the present invention, a methyl, isopropyl or tert-butyl group is preferable.

The term "alkenyl group(s) having 2 to 6 carbon atoms which may be branched or form a cyclic group" means any of linear, branched or cyclic alkenyl group(s) having 2 to 6 carbon atoms, including an ethenyl, propenyl, isopropenyl, cyclopropenyl, butenyl, 1-methyl-1-propenyl, 1-methyl-2-propenyl, 2-methyl-1-propenyl, 2-methyl-2-propenyl, cyclobentyl, penthenyl, cyclopenthenyl, hexthenyl and cyclohexthenyl group. In the present invention, a propenyl or a butenyl group is preferable.

The term "alkynyl group(s) having 2 to 6 carbon atoms and which may be branched or form a cyclic group" means any of linear, branched or cyclic alkynyl group(s) having 2 to 6 carbon atoms, including an ethynyl, propynyl, cycloproplethynyl, butynyl, 1-methyl-2-propynyl, pentynyl, cyclobutylethynyl, hexynyl, and trimethylsilylethynyl group. In the present invention, an ethynyl or trimethylsilylethynyl group is preferable.

The term "allyl or substituted allyl group(s) having 3 to 9 carbon atoms which may be branched or form a cyclic group" means allyl group(s), or any of substituted allyl group(s) having a substituent in 1 and/or 2 and/or 3 site and having total carbon atoms of 4 to 9, including a 2-butenyl, 1-cyclopentenylmethyl, and 3-methyl-2-butenyl group. In the present invention, an allyl group is preferarable.

The term "propargyl or substituted propargyl group(s) which having 3 to 9 carbon atoms which may be branched" means propargyl group, or any of substituted propargyl group(s) having substituent in 1 and/or 3 site and having 4 to 9 of total carbon atoms. The example includes 2-butynyl and 3-trimethylsilyl-2-propynyl. In the present invention, propargyl and 3-trimethylsilyl-2-propynyl are preferred.

The term "a functional group having leaving ability" means an atom or an atomic group which is eliminated from a reaction substrate, in other words, a leaving group, in a substitution reaction or an elimination reaction. Examples of the group include a halogen atom and a sulfonyloxy group.

The "aralkyl group" used in the present invention includes a benzyl, phenethyl, naphthylmethyl and anthracenylmethyl group.

The "heteroaralkyl group" used in the present invention includes a pyridylmethyl, quinonylmethyl, indolylmethyl, furylmethyl, thienylmethyl and pyrolylmethyl group.

The "aryl group" used in the present invention includes a phenyl, biphenyl, naphthyl and anthracenyl group.

The "heteroaryl group" used in the present invention includes a pyridyl, quinolyl, pyrrolyl, imidazolyl, furyl, indolyl, thienyl, oxazoyl, and thiazolyl group.

The "halogen atom" used in the present invention includes a chlorine, bromine and iodine atom.

The "sulfonyloxy group" used in the present invention includes a methanesulfonyloxy, p-toluenesulfonyloxy and trifluoromethane sulfonyloxy group.

An appropriate solvent includes benzene, toluene, xylene, ethylether, isopropylether, tetrahydrofuran, dioxane, or the like. Among them, two phase system comprising water immissible solvent and water. The inorganic base includes lithium hydroxide, sodium hydroxide, potassium hydroxide, calcium hydroxide, rubidium hydroxide, cesium hydroxide or the like.

The inventor has found that optically active quarternary ammonium salts expressed by the general formula (I) that can form a spiro structure and an axial chirality, functions as an excellent phase-transfer catalyst in the two-phase medium including organic solvent and water:

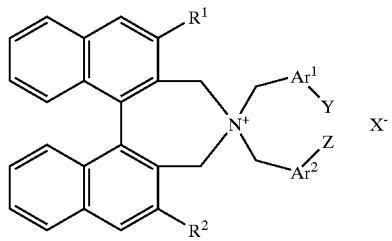

wherein $R^1$ and $R^2$ are groups independently selected from the group consisting of a hydrogen atom; an alkyl group having 1 to 6 carbon atoms which may be branched or form a cyclic group; an alkenyl group having 2 to 6 carbon atoms which may be branched or form a cyclic group; an alkynyl group having 2 to 6 carbon atoms which may contain branched or cyclic structure; an aralkyl group which may be substituted with an alkyl group having 1 to 4 carbon atoms, an alkoxy group having 1 to 3 carbon atoms or a halogen atom; a heteroaralkyl group which may be substituted with an alkyl group having 1 to 4 carbon atoms, an alkoxy group having 1 to 3 carbon atoms or a halogen atom; an aryl group which may be substituted with an alkyl group having 1 to 4 carbon atoms, an alkoxy group having 1 to 3 carbon atoms or a halogen atom; a heteroaryl group which may be substituted with an alkyl group having 1 to 4 carbon atoms, an alkoxy group having 1 to 3 carbon atoms or a halogen atom; a ($C_1$ to $C_3$ alkoxy) carbonyl group; a carbamoyl group; a N—($C_1$ to $C_4$ alkyl) carbamoyl group; and a N,N—di($C_1$ to $C_4$ alkyl) carbamoyl group (wherein alkyl may be the same or different), and $R^1$ and $R^2$ may be the same or different; $Ar^1$ and $Ar^2$ are groups independently selected from the group consisting of an aryl group which may be substituted with an alkyl group having 1 to 4 carbon atoms, an alkoxy group having 1 to 3 carbon atoms or a halogen atom; and a heteroaryl group which may be substituted with an alkyl group having 1 to 4 carbon atoms, an alkoxy group having 1 to 3 carbon atoms or a halogen atom, and $Ar^1$ and $Ar^2$ may be the same or different; $X^-$ is a halide anion; and Y and Z are groups independently selected from the group consisting of a hydrogen atom; a halogen atom; an alkyl group having 1 to 4 carbon atoms; and an alkoxy group having 1 to 3 carbon atoms, and Y and Z may be the same or different or may form a single bond.

The inventor has found that, by using the optically active quarternary ammonium salt expressed by the general formula (I), an optically active α-amino acid derivative expressed by the general formula (XXI) having high optical purity is produced:

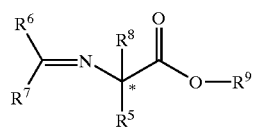

XXI wherein $R^5$ is an alkyl group having 1 to 6 carbon atoms which may be branched or form a cyclic group; an allyl or substituted allyl group having 3 to 9 carbon atoms which may be branched or form a cyclic group; an aralkyl group which may be substituted with an alkyl group having 1 to 4 carbon atoms, an alkoxy group having 1 to 3 carbon atoms, a halogen atom, an aryl group which may be substituted with an alkyl group having 1 to 4 carbon atoms, an alkoxy group having 1 to 3 carbon atoms or a halogen atom or a heteroaryl group which may be substituted with an alkyl group having 1 to 4 carbon atoms, an alkoxy group having 1 to 3 carbon atoms or a halogen atom; a heteroaralkyl group which may be substituted with an alkyl group having 1 to 4 carbon atoms, an alkoxy group having 1 to 3 carbon atoms, a halogen atom, an aryl group which may be substituted with an alkyl group having 1 to 4 carbon atoms, an alkoxy group having 1 to 3 carbon atoms or a halogen atom, or a heteroaryl group which may be substituted with an alkyl group having 1 to 4 carbon atoms, an alkoxy group having 1 to 3 carbon atoms or a halogen atom; or a propargyl or substituted propargyl group which has 3 to 9 carbon atoms that may be branched;

$R^6$ and $R^7$ are the same or different and are hydrogen atoms, an aryl group which may be substituted with an alkyl group having 1 to 3 carbon atoms, an alkoxy group having 1 to 3 carbon atoms or a halogen atom, with the proviso that they are not both hydrogen atoms;

$R^8$ is a hydrogen atom; an aryl group which may be substituted with an alkyl group having 1 to 3 carbon atoms, an alkoxy group having 1 to 3 carbon atoms or a halogen atom; an alkyl group having 1 to 6 carbon atoms which may be branched or form a cyclic group; an aralkyl group which may be substituted with an alkyl group having 1 to 3 carbon atoms, an alkoxy group having 1 to 3 carbon atoms or a halogen atom;

and $R^9$ is an alkyl group having 1 to 4 carbon atoms; and
* is a newly produced chiral center;
by stereoselectively alkylating a glycine derivative expressed by the general formula (XIX):

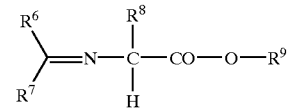

XIX wherein $R^6$ and $R^7$ are the same or different and are hydrogen atoms, an aryl group which may be substituted with alkyl group having 1 to 3 carbon atoms, alkoxy group having 1 to 3 carbon atoms or a halogen atom, with proviso that they are not both hydrogen atoms; $R^8$ is a hydrogen atom; an aryl group which may be substituted with an alkyl group having 1 to 3 carbon atoms, an alkoxy group having 1 to 3 carbon atoms or a halogen atom; an alkyl group having 1 to 6 carbon atoms which may be branched or form a cyclic group; an aralkyl group which may be substituted with an alkyl group having 1 to 3 carbon atoms, an alkoxy group having 1 to 3 carbon atoms or a halogen atom; and $R^9$ is an alkyl group having 1 to 4 carbon atoms;
with a compound expressed by the general formula (XX):

$$R^5—W \qquad (XX)$$

wherein $R^5$ is an alkyl group having 1 to 6 carbon atoms which may be branched or form a cyclic group; an allyl or substituted allyl group having 3 to 9 carbon atoms which may be branched or form a cyclic group; an aralkyl group which may be substituted with an alkyl group having 1 to 4 carbon atoms, an alkoxy group having 1 to 3 carbon atoms, a halogen atom, an aryl group which may be substituted with an alkyl group having 1 to 4 carbon atoms, an alkoxy group having 1 to 3 carbon atoms or a halogen atom, or a heteroaryl group which may be substituted with an alkyl group having 1 to 4 carbon atoms, an alkoxy group having 1 to 3 carbon atoms or a halogen atom; a heteroaralkyl group which may be substituted with an alkyl group having 1 to 4 carbon atoms, an alkoxy group having 1 to 3 carbon atoms, a halogen atom, an aryl group which may be substituted with an alkyl group having 1 to 4 carbon atoms, an alkoxy group having 1 to 3 carbon atoms or a halogen atom, or a heteroaryl group which may be substituted with an alkyl group having 1 to 4 carbon atoms, an alkoxy group having 1 to 3 carbon atoms or a halogen atom; a propargyl or substituted propargyl group which has 3 to 9 carbon atoms that may be branched; and W is a functional group having an ability to eliminate sulfonyloxy group and the like.

In the optically active quarternary ammonium salt with the axial chirality expressed by the general formula (I), when the spiro type quarternary ammonium salts with the axial chirality expressed by the general formula (II) are employed as phase-transfer catalyst, a higher stereoselective alkylation can be performed:

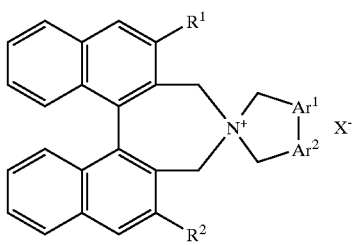

II wherein $R^1$ and $R^2$ are groups independently selected from the group consisting of a hydrogen atom; an alkyl group having 1 to 6 carbon atoms which may be branched or form a cyclic group; an alkenyl group having 2 to 6 carbon atoms which may be branched or form a cyclic group; an alkynyl group having 2 to 6 carbon atoms which may contain branched or cyclic structure; an aralkyl group which may be substituted with an alkyl group having 1 to 4 carbon atoms, an alkoxy group having 1 to 3 carbon atoms or a halogen atom; a heteroaralkyl group which may be substituted with an alkyl group having 1 to 4 carbon atoms, an alkoxy group having 1 to 3 carbon atoms or a halogen atom; an aryl group which may be substituted with an alkyl group having 1 to 4 carbon atoms, an alkoxy group having 1 to 3 carbon atoms or a halogen atom; a heteroaryl group which may be substituted with an alkyl group having 1 to 4 carbon atoms, an alkoxy group having 1 to 3 carbon atoms or a halogen atom; a ($C_1$ to $C_3$ alkoxy) carbonyl group; a carbamoyl group; a N—($C_1$ to $C_3$ alkyl) carbamoyl group; and a N,N—di($C_1$ to $C_4$ alkyl) carbamoyl group (wherein alkyl may be the same or different), and $R^1$ and $R^2$ may be the same or different;

$Ar^1$ and $Ar^2$ are groups independently selected from the group consisting of an aryl group which may be substituted with an alkyl group having 1 to 4 carbon atoms, an alkoxy group having 1 to 3 carbon atoms or a halogen atom; and a heteroaryl group which may be substituted with an alkyl group having 1 to 4 carbon atoms, an alkoxy group having 1 to 3 carbon atoms or a halogen atom, and $Ar^1$ and $Ar^2$ may be the same or different;

$X^-$ is a halide anion.

Particularly, in the compound of general formula (II), optically active spiro type quarternary ammonium salt (in which $Ar^1$ and $Ar^2$ are β-naphthyl groups, each $Ar^1$ and $Ar^2$ is bound to α-=site of the other group, and $X^-$ is a bromide anion) having $C_2$-symmetric axial chirality expressed by the general formula (III):

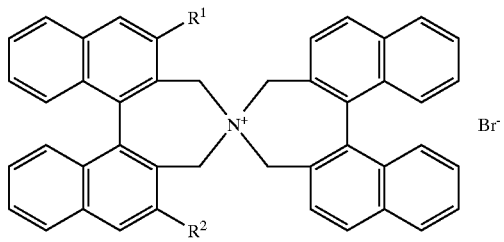

III wherein $R^1$ and $R^2$ are groups independently selected from the group consisting of a hydrogen atom; an alkyl group having 1 to 6 carbon atoms which may be branched or form a cyclic group; an alkenyl group having 2 to 6 carbon atoms which may be branched or form a cyclic group; an alkynyl group having 2 to 6 carbon atoms which may contain branched or cyclic structure; an aralkyl group which may be substituted with an alkyl group having 1 to 4 carbon atoms, an alkoxy group having 1 to 3 carbon atoms or a halogen atom; a heteroaralkyl group which may be substituted with an alkyl group having 1 to 4 carbon atoms, an alkoxy group having 1 to 3 carbon atoms or a halogen atom; an aryl group which may be substituted with an alkyl group having 1 to 4 carbon atoms, an alkoxy group having 1 to 3 carbon atoms or a halogen atom; a heteroaryl group which may be substituted with an alkyl group having 1 to 4 carbon atoms, an alkoxy group having 1 to 3 carbon atoms or a halogen atom; a ($C_1$ to $C_3$ alkoxy) carbonyl group; a carbamoyl group; a N—($C_1$ to $C_4$ alkyl) carbamoyl group; and a N,N—di($C_1$ to $C_4$ alkyl) carbamoyl group (wherein alkyl may be the same or different); $R^1$ and $R^2$ may be the same or different; and, in particular, both $R^1$ and $R^2$ are phenyl, or both $R^1$ and $R^2$ are β-naphthyl;

are used as particularly useful phase-transfer catalyst, thereby providing the above-mentioned stereoselective alkylation of 90% e.e. or more.

The optically active quarternary ammonium salt, with an axial chirality and which may form a spiro structure, expressed by the general formula (I) can be produced by reacting an optically active dinaphthoazepine derivative with an axial chirality, expressed by the general formula (IV):

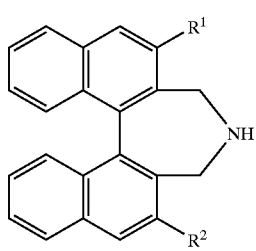

IV wherein $R^1$ and $R^2$ are groups independently selected from the group consisting of a hydrogen atom; an alkyl group having 1 to 6 carbon atoms which may be branched or form a cyclic group; an alkenyl group having 2 to 6 carbon atoms which may be branched or form a cyclic group; an alkynyl group having 2 to 6 carbon atoms which may contain branched or cyclic structure; an aralkyl group which may be substituted with an alkyl group having 1 to 4 carbon atoms, an alkoxy group having 1 to 3 carbon atoms or a halogen atom; a heteroaralkyl group which may be substituted with an alkyl group having 1 to 4 carbon atoms, an alkoxy group having 1 to 3 carbon atoms or a halogen atom; an aryl group which may be substituted with an alkyl group having 1 to 4 carbon atoms, an alkoxy group having 1 to 3 carbon atoms or a halogen atom; a heteroaryl group which may be substituted with an alkyl group having 1 to 4 carbon atoms, an alkoxy group having 1 to 3 carbon atoms or a halogen atom; ($C_1$ to $C_3$ alkoxy) carbonyl group; a carbamoyl group; a N—($C_1$ to $C_4$ alkyl) carbamoyl group; and a N,N—di($C_1$ to $C_4$ alkyl) carbamoyl group (wherein alkyl may be the same or different), and $R^1$ and $R^2$ may be the same or different;

with a compound of general formula (V):

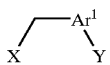

V and a compound of general formula (VI):

VI wherein, in the general formulae (V) and (VI), $Ar^1$ and $Ar^2$ are groups independently selected from the group consisting of an aryl group (such as phenyl, biphenyl, naphthyl) which may be substituted with an alkyl group having 1 to 4 carbon atoms, an alkoxy group having 1 to 3 carbon atoms or a halogen atom; and a heteroaryl group (such as pyridyl, quinonyl) which may be substituted with an alkyl group having 1 to 4 carbon atoms, an alkoxy group having 1 to 3 carbon atoms or a halogen atom, and $Ar^1$ and $Ar^2$ may be the same or different;

X is a halogen atom; and

Y and Z are groups independently selected from the group consisting of a hydrogen atom; a halogen atom; an alkyl group having 1 to 4 carbon atoms; and an alkoxy group having 1 to 3 carbon atoms, and Y and Z may be the same or different or may form a single bond;

in this order or simultaneously, in the presence of an acid capturing agent and in an appropriate solvent.

The compound of general formula (IV) can be produced by subjecting the compound of general formula (VIII) to a method of Hawkins, J. M. et al. (Hawkins, J. M. et al., J. Org. Chem., 1994, 59, 649). A number of the compounds expressed by the general formulae (V) and (VI) are commercially available as a reagent. Alternatively, the compound of general formula (VIII) may be used in place of these compounds.

According to the present invention, a compound of general formula (I) can be produced by stirring a compound of general formula (IV) and (V) and (VI) in an alcoholic solvent in the presence of an acid capturing agent at an appropriate temperature. Compound (V) and (VI) can be used preferably 0.8 to 1.5 equivalents, more preferably 1.0 to 1.4 equivalents and most preferably 1.1 to 1.2 equivalents to the compound of the general formula (IV), respectively. The example of the alcohol includes methanol, ethanol, propanol, isopropylalcohol, butanol and tert-butylalcohol. Example of the acid capturing agent includes potassium carbonate and sodium carbonate. The temperature can be between room temperature and a boiling temperature of the solvent used, preferably between room temperature and 80° C. The stirring period can be preferably 30 minutes to 12 hours, more preferably 2 to 11 hours and most preferably 3 to 10 hours. In the reaction, above-mentioned solvent may be used preferably 5 to 50 times, more preferably 10 to 40 times of volume (mL) based on the weight (g) of compound of general formula (IV). The acid capturing agent may be used preferably 2 to 4 equivalents and more preferably 2 to 3 equivalents to the compound of general formula (IV).

The optically active spiro type quarternary ammonium salt with an axial chirality and expressed by the general formula (II) can be produced by reacting a compound of general formula (IV) with a compound of general formula (VII):

VII wherein $Ar^1$ and $Ar^2$ are groups independently selected from the group consisting of an aryl group such as phenyl, biphenyl, naphthyl group which may be substituted with an alkyl group having 1 to 4 carbon atoms, an alkoxy group having 1 to 3 carbon atoms or a halogen atom; and a heteroaryl group such as a pyridyl group or quinonyl group which may be substituted with an alkyl group having 1 to 4 carbon atoms, an alkoxy group having 1 to 3 carbon atoms or a halogen atom;

$Ar^1$ and $Ar^2$ may be the same or different; and

X is a halogen atom;

in the presence of an acid capturing agent in an appropriate solvent.

According to the preset invention, a compound of general formula (II) can be produced by stirring a compound of general formula (IV) and (VII) in an alcohol solvent in the presence of an acid capturing agent at an appropriate temperature. The compound of general formula (VII) can be used preferably 1 to 3 equivalents, more preferably 1 to 2 equivalents and most preferably 1 to 1.5 equivalents to the compound of general formula (IV). Example of the alcohol includes methanol, ethanol, propanol, isopropylalcohol, butanol and tert-butylalcohol. Example of the acid capturing agent includes potassium carbonate and sodium carbonate. The temperature can be between room temperature and a boiling point of the solvent used, preferably between room temperature and 80° C. The stirring period can be preferably 30 minutes to 12 hours, more preferably 1 to 11 hours and most preferably 2 to 10 hours.

In the reaction, above-mentioned solvent may be used preferably 5 to 50 times, more preferably 5 to 30 times and most preferably 10 to 25 times of volume (mL) based on the weight of the compound of general formula (IV). The acid capturing agent may be used at the weight of preferably 2 to 4 equivalents and more preferably 2 to 3 equivalents to the compound of general formula (IV).

The optically active spiro type quarternary ammonium salt with an axial chirality and expressed by the general formula (III) can be produced by reacting optically active 3,5-dihydro-4H-dinaphtho[2,1-c:1',2'-e] azepine expressed by the general formula (IX) with optically active 1,1'-binaphthyl derivative expressed by the general formula (X):

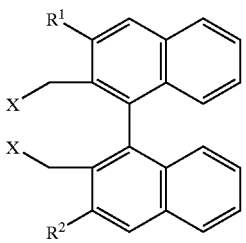

X

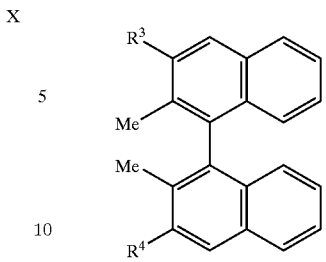

XI wherein $R^1$ and $R^2$ are groups independently selected from the group consisting of a hydrogen atom; an alkyl group having 1 to 6 carbon atoms which may be branched or form a cyclic group; an alkenyl group having 2 to 6 carbon atoms which may be branched or form a cyclic group; an alkynyl group having 2 to 6 carbon atoms which may contain branched or cyclic structure; an aralkyl group which may be substituted with an alkyl group having 1 to 4 carbon atoms, an alkoxy group having 1 to 3 carbon atoms or a halogen atom; a heteroaralkyl group which may be substituted with an alkyl group having 1 to 4 carbon atoms, an alkoxy group having 1 to 3 carbon atoms or a halogen atom; an aryl group which may be substituted with an alkyl group having 1 to 4 carbon atoms, an alkoxy group having 1 to 3 carbon atoms or a halogen atom; a heteroaryl group which may be substituted with an alkyl group having 1 to 4 carbon atoms, an alkoxy group having 1 to 3 carbon atoms or a halogen atom; a ($C_1$ to $C_3$ alkoxy) carbonyl group; a carbamoyl group; a N—($C_1$ to $C_4$ alkyl) carbamoyl group; and a N,N—di($C_1$ to $C_4$ alkyl) carbamoyl group (wherein alkyl may be the same or different), and $R^1$ and $R^2$ may be the same or different; and; X is a halogen atom; in alcoholic solvent in the presence of inorganic base as an acid capturing agent.

The optically active 3,5-dihydro-4H-dinaphtho[2,1-c:1', 2'-e]azepine (IX) can be produced by the method of Hawkins et al (Hawkins, J. M. et al., J. Org. Chem. 1994, 59, 649).

According to the present invention, a compound of general formula (III) can be produced by stirring a compound of general formula (IX) with a compound of general formula (X) in an alcoholic solvent in the presence of an acid capturing agent at an appropriate temperature.

The compound of general formula (X) can be used preferably 1 to 3 equivalents, more preferably 1 to 2 equivalents and most preferably 1 to 1.5 equivalents to the compound of general formula (IX). Example of the alcohol includes methanol, ethanol, propanol, isopropylalcohol, butanol and tert-butylalcohol. Example of the acid capturing agent includes potassium carbonate and sodium carbonate. The temperature can be between room temperature and a boiling point of the solvent used, preferably between room temperature and 80° C.

The stirring period can be preferably 30 minutes to 12 hours, more preferably 1 to 11 hours and most preferably 2 to 10 hours. In the reaction, above-mentioned solvent may be used preferably 5 to 50 times, and more preferably 5 to 30 times of volume (mL) based on the weight (g) of the compound of general formula (IX). The acid capturing agent may be used at the weight of preferably 2 to 4 equivalents and more preferably 2 to 3 equivalents to the compound of general formula (IX).

The compound expressed by the general formula (X) can be produced by reacting the optically active 2,2'-dimethyl-1,1'-binaphthyl derivative expressed by the general formula (XI):

wherein $R^3$ and $R^4$ are groups independently selected from the group consisting of a hydrogen atom; an alkyl group having 1 to 6 carbon atoms which may be branched or form a cyclic group; an alkenyl group having 2 to 6 carbon atoms which may be branched or form a cyclic group; an alkynyl group having 2 to 6 carbon atoms which may contain branched or cyclic structure; an aralkyl group which may be substituted with an alkyl group having 1 to 4 carbon atoms, an alkoxy group having 1 to 3 carbon atoms or a halogen atom; a heteroaralkyl group which may be substituted with an alkyl group having 1 to 4 carbon atoms, an alkoxy group having 1 to 3 carbon atoms or a halogen atom; an aryl group which may be substituted with an alkyl group having 1 to 4 carbon atoms, an alkoxy group having 1 to 3 carbon atoms or a halogen atom; a heteroaryl group which may be substituted with an alkyl group having 1 to 4 carbon atoms, an alkoxy group having 1 to 3 carbon atoms or a halogen atom; a ($C_1$ to $C_3$ alkoxy) carbonyl group; a carbamoyl group; a N—($C_1$ to $C_4$ alkyl) carbamoyl group; and a N,N—di($C_1$ to $C_4$ alkyl) carbamoyl group (wherein alkyl may be the same or different), and $R^3$ and $R^4$ may be the same or different;
with an appropriate halogenating agent (halogen radical generating agent) which can generate a halogen radical in an appropriate solvent and in the presence of appropriate radical reaction initiator to halogenate both 2- and 2'-methyl groups.

According to the present invention, a compound of general formula (X) can be produced by stirring a compound of general formula (XI) with a radical reaction generating agent in the presence of radical reaction initiator in a hydrocarbon solvent at an appropriate temperature.

The compound of the general formula (XI) can be used preferably 2 to 3 equivalents and more preferably 2 to 2.5 equivalents to the halogen radical reaction generating agent. Example of the radical reaction generating agent includes a N-bromosuccinimide. Example of the halogen radical reaction initiator includes benzoyl peroxide. Example of the hyrocarbon solvent includes hexane, cyclohexane and petroleum ether. The stirring temperature is between room temperature and a boiling point of the solvent used, preferably between 60° C. and 100° C. The stirring period can be preferably 30 minutes to 5 hours, more preferably 1 to 5 hours and most preferably 1 to 3.5 hours. In the reaction, the solvent may be used preferably 5 to 20 times, more preferably 5 to 15 times and most preferably 5 to 10 times of volume (mL) based on weight of the compound of general formula (XI). The radical reactin initiator may be used preferably 0.1 to 0.6 equivalents and more preferably 0.2 to 0.6 equivalents to the compound of general formula (XI). The halogen radical reaction initiator may be used preferably 1 to 5 equivalents, more preferably 1.5 to 3.5 equivalents and most preferably 1.8 to 2.6 equivalents to the compound of general formula (XI).

A compound expressed by the general formula (XI) can be produced by reacting the optically active 2,2'- bistrifluoromethanesulfonyloxy-1,1'-binaphthyl derivative expressed by the general formula (XII):

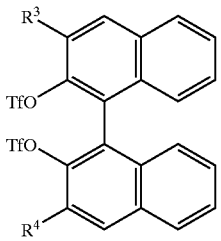

(XII)

wherein $R^3$ and $R^4$ are groups independently selected from the group consisting of a hydrogen atom; an alkyl group having 1 to 6 carbon atoms which may be branched or form a cyclic group; an alkenyl group having 2 to 6 carbon atoms which may be branched or form a cyclic group; an alkynyl group having 2 to 6 carbon atoms which may contain branched or cyclic structure; an aralkyl group which may be substituted with an alkyl group having 1 to 4 carbon atoms, an alkoxy group having 1 to 3 carbon atoms or a halogen atom; an aryl group which may be substituted with an alkyl group having 1 to 4 carbon atoms, an alkoxy group having 1 to 3 carbon atoms or a halogen atom; a heteroaryl group which may be substituted with an alkyl group having 1 to 4 carbon atoms, an alkoxy group having 1 to 3 carbon atoms or a halogen atom; a ($C_1$ to $C_3$ alkoxy) carbonyl group; a carbamoyl group; a N—($C_1$ to $C_3$ alkyl) carbamoyl group; and a N,N—di($C_1$ to $C_3$ alkyl) carbamoyl group (wherein alkyl may be the same or different), and $R^3$ and $R^4$ may be the same or different; and Tf is a trifluormethanesulfonyl group;

with methylmagnesium halide expressed by the general formula (XIII):

 MeMgX (XIII)

wherein X is a halogen atom; in the presence of a nickel catalyst and in an appropriate solvent.

According to the present invention, a compound of general formula (XI) can be produced by stirring a compound of general formula (XII) with compound (XIII) in the presence of a nickel catalyst in an ether solvent at an appropriate temperature.

The compound (XIII) can be used preferably 2 to 7 equivalents and more preferably 2.5 to 6.5 equivalents to the compound of general formula (XII). Example of the compound (XIII) includes MeMgCl. Example of the nickel catalyst includes $NiCl_2(PPh_3)_2$. Example of the ether solvent includes ether, isopropylether, butylether, THF and tert-butylmethylether. The temperature can be between −15° C. and a boiling point of the solvent used preferably between 0° C. and 50° C. The stirring period can be preferably 2 to 50 hours and more preferably 5 to 40 hours. In the reaction, solvent may be used preferably 5 to 20 times, more preferably 7 to 15 times of volume (mL) based on the weight of the compound of the general formula (XII). The nickel catalyst may be used at the weight of preferably 0.01 to 0.1 equivalents and more preferably 0.02 to 0.06 equivalents to the compound of general formula (XII).

When $R^3$ and $R^4$ are functional groups other than hydrogen atom, the compound (XII) can be produced by applying a method catalyzed by palladium such a carbonylation reaction, Heck reaction, Stille reaction, Sonogashira reaction or Suzuki reaction to an optically active 3,3'-dibromo-2,2'-bistrifluoromethane-sulfonyloxy-1,1'-binaphthyl derivative expressed by formula (XIV):

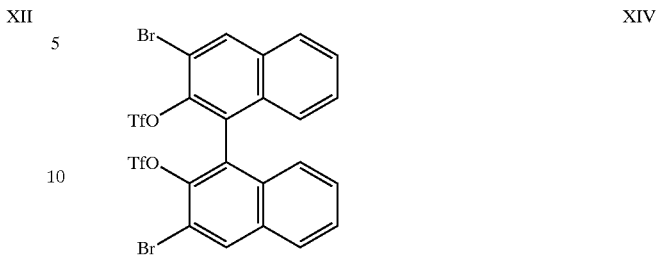

wherein Tf is a trifluoromethanesulfonyl group;

Particularly, the compound expressed by the general formula (XVII):

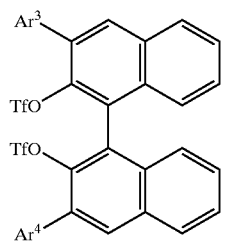

(XVII)

wherein $Ar^3$ and $Ar^4$ are groups selected from the group consisting of an alkenyl group having 2 to 6 carbon atoms which may be branched or form a cyclic group; an aryl group which may be substituted with an alkyl group having 1 to 4 carbon atoms, an alkoxy group having 1 to 3 carbon atoms or a halogen atom; and a heteroaryl group which may be substituted with an alkyl group having 1 to 4 carbon atoms, an alkoxy group having 1 to 3 carbon atoms or a halogen atom, and $Ar^3$ and $Ar^4$ may be the same or different; can be produced by reacting the compound (XIV) with a compound of general formula (XV):

 $Ar^3B(OH)_2$ (XV)

and a compound of general formula (XVI):

 $Ar^4B(OH)_2$ (XVI)

wherein, in the general formulae (XV) and (XVI), $Ar^3$ and $Ar^4$ are groups selected from the group consisting of an alkenyl group having 2 to 6 carbon atoms which may be branched or form a cyclic group; an aryl group which may be substituted with an alkyl group having 1 to 4 carbon atoms, an alkoxy group having 1 to 3 carbon atoms or a halogen atom; and a heteroaryl group which may be substituted with an alkyl group having 1 to 4 carbon atoms, an alkoxy group having 1 to 3 carbon atoms, or a halogen atom, and $Ar^3$ and $Ar^4$ may be the same or different; in this order or simultaneously, in an appropriate solvent and in the presence of base and palladium catalyst.

According to the present invention, the compound of the general formula (XVII) can be produced by stirring a compound of the general formula (XIV) with a compound of the general formula (XV) and a compound of the general formula (XVI) in an ether solvent or DMF in the presence of a palladium catalyst and a base at an appropriate temperature.

The compounds of the general formulae (XV) and (XVI) can be used preferably 1.2 to 3 equivalents, more preferably 1.2 to 2.0 equivalents and most preferably 1.25 to 1.75 equivalents to the compound of the general formula (XIV), respectively. Example of the ether solvent includes ether, isopropylether, butylether, THF and tert-butylmethylether. Example of the base includes sodium bicarbonate, lithium hydroxide, sodium hydroxide, potassium hydroxide, thallium hydroxide, sodium methoxide, sodium ethoxide and potassium phosphate (hydrate). The palladium catalyst can be added preferably 0.01 to 0.1 equivalents, more preferably 0.02 to 0.08 equivalents and most preferably 0.03 to 0.06 equivalents to the compound (XIV). The temperature can be between room temperature and a boiling point of the solvent used, preferably between room temperature and 100° C. The stirring can be preferably 1 to 20 hours, more preferably 3 to 15 hours and most preferably 6 to 12 hours. In the reaction, solvent may be used preferably 5 to 20 times and more preferably 6 to 12 times of volume (mL) based on the weight of the compound of general formula (XIV). The base may be used preferably 2 to 5 equivalents and more preferably 2.5 to 3.5 equivalents to the compound of general formula (XIV). Example of the palladium catalyst includes 0 equivalent of palladium complex such as $Pd(PPh_3)_4$ and a catalyst generated in the reaction solvent by $Pd(OAc)_2$ and $PPh_3$. In the latter example, the ratio of $Pd(OAc)_2$ tp $PPh_3$ can be from 1:4 to 1:5.

A compound (XIV) can be produced by reacting an optically active 2,2'-dibromo-1,1'-bi-2-naphthol expressed by formula (XVIII):

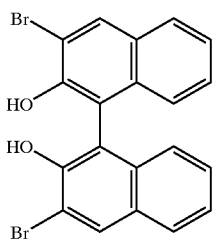

XVIII with a triflatating agent in an inert solvent in the presence of base at a temperature from −78° C. to 0° C. Example of the inert solvent includes toluene, methylene chloride, THF and DMF. The base can be used preferably 2 to 4 equivalents, more preferably 2.5 to 3.3 equivalents to the compound (XVIII). Example of the triflatating agent includes trifluoromethanesulfonic anhydride and trifluoromethanesulfinyl chloride. The triflatating agent can be used preferably 2 to 2.5 equivalents, more preferably 2.2 to 2.5 equivalents to the compound (XVIII). In this reaction, the reaction solvent may be used preferably 5 to 20 times and more preferably 6 to 15 times of volume (mL) based on the weight of the compound of general formula (XV). Example of the base includes tertiary amine such as triethylamine, N,N-dimethylisopropylamine and N-methylmorpholine.

The optically active quaternary ammonium salts (I) to (III) produced by the above methods having axial chirality and able to form spiro type structure are useful as a phase-transfer catalyst for stereoselective alkylation of the compound (IX).

The compound of general formula (I) is pure regarding axial chirality, and used as a phase-transfer catalyst. The term "pure regarding axial chirality" means that the percentage of one of the isomer is larger than the percentage of other isomers in a variety of isomers based on the axial chirality. The percentage of the one of the isomer is 90% or more, preferably 95% or more, and even more preferably 98% or more.

According to the present invention, an optically active compound (XXI) can be produced by stirring a compound (XIX) with any one of compounds (I) to (III) that can act as a phase-transfer catalyst in two-phase mixture comprising a hydrocarbon solvent and an alkaline aqueous solution at an appropriate temperature. The compound (XX) can be added preferably 1 to 1.5 equivalents, more preferably 1.1 to 1.3 equivalents and most preferably 1.2 to 1.25 equivalents to the compound (XIX). The compound (I) to (III) can be added preferably 0.005 to 0.03 equivalents and more preferably 0.0075 to 0.0125 equivalents to the compound (XIX). The temperature can be between −10° C. and room temperature, preferably between −5° C. and +5° C. The stirring period can be preferably 15 minutes to 3 hours, more preferably 0.5 to 2 hours and most preferably 0.5 to 15. hours. Using above-mentioned methods, optically active compound (XXI) can be produced with high yield and high optical purity.

The hydrocarbon solvent used in the present invention includes any type of solvent which is immiscible to water, and includes hexane, toluene or the like. The solvent may be used preferably 5 to 30 times and more preferably 8 to 25 times of volume (mL) based on the weight of the compound of general formula (XIX). The alkaline aqueous solution may be used as 10 to 60% aqueous solution of alkaline metal hydroxide such as lithium hydroxide, potassium hydroxide, sodium hydroxide, cesium hydroxide, rubidium hydroxide or the like. The alkaline aqueous solution may be used at the ratio of volume (mL) to weight (g) of preferably 4 to 20 times and more preferably 8 to 15 times based on the compound of general formula (XIX).

For example, for the synthesis of (S)-form of the compound (XXI), compound (I) with an axial chirality of (S) can be used. On the other hand, for the synthesis of (R) form, compound (I) with an axial chirality of (R) can be used.

The term "high optical purity" used herein means optical purity of preferably 90% e.e. or more and more preferably 95% e.e.

EXAMPLES

Hereinafter, the present invention will be described more specifically by way of examples. However, the present invention is not limited by the Examples.

Example 1

Preparation of (S)-1,1'-bi-3-bromo-2-trifluoromethanesulfonyloxy

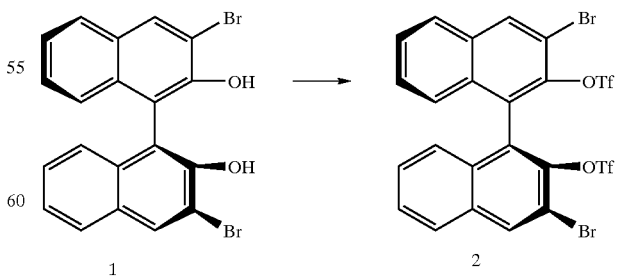

Under argon atmosphere, triethylamine (6.54 mL, 42 mmol) was added to a solution of (S)-1,1'-bi-3-bromo-2- naphthol (1) (6.19 g, 14 mmol) in dichloromethane solution (40 mL) at room temperature, and cooled to −78° C. Then, trifluoromethanesulfonic anhydride (5.16 mL, 31 mmol) was added dropwise, and the mixture was stirred for 2 hours under the same cooling conditions. The reaction mixture was poured into a saturated NH$_4$Cl aqueous solution, and the mixture was extracted with dichloromethane. The dichloromethane extract was dried over Na$_2$SO$_4$, and concentrated under vacuum. The residue was chromatographed over silica gel. Elution with dichloromethane—hexane (1:5) gave (S)-1,1'-bi-3-bromo-2-trifluoromethanesulfonyloxynaphthyl (2) (9.90 g, 14 mmol) in a quantitative yield.

300 MHz $^1$H-NMR(CDCl$_3$): δ8.44(2H, s, Ar—H), 7.92 (2H, d, J=8.1 Hz, Ar—H), 7.61(2H, ddd, J=1.2, 6.9, 8.1 Hz, Ar—H), 7.41(2H, ddd, J=1.2, 6.9, 8.1 Hz, Ar—H), 7.22(2H, d, J=8.1 Hz, Ar—H) ppm.

Example 2

Preparation of (S)-1,1'-bi-3-(β-naphthyl)-2-trifuloromethane sulfonyloxynaphthyl (3)

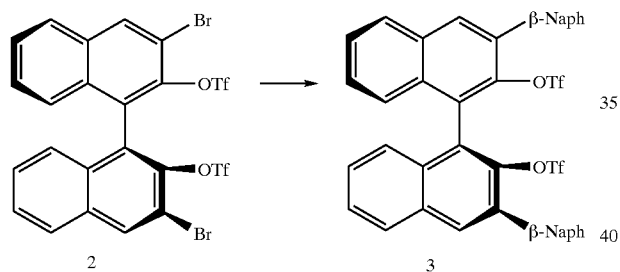

The mixture of (S)-1,1'-bi-3-bromo-2-trifluoromethanesulfonyl oxynaphthyl (2) 3.54 g, 5.0 mmol), β-naphthylboronic acid (β-C$_{10}$H$_7$B(OH)$_2$; 2.94 g, 15 mmol), palladium acetate [Pd(OAC)$_2$; 57.9 mg, 5 mol %], triphenylphosphine (0.294 g, 22 mol %), potassium phosphate hydrate (4.29 g, 15 mmol) and THF (25 mL) was stirred and heated at 65° C. for 10 hours. Then, the reaction mixture was poured into a saturated NH$_4$Cl aqueous solution. The palladium catalyst was filtered off, and the filtrate was extracted with ether. The ether extract was dried over Na$_2$SO$_4$, and concentrated under vacuum. The residue was subjected to a silica gel chromatography, and elution with ether—dichloromethane—hexane (1:2:60) gave (S)-1,1'-bi-3-(β-naphthyl)-2-trifluoromethanesulfonyloxy-naphthyl (3) (2.85 g, 4.0 mmol) in 80% yield.

300 MHz $^1$H-NMR(CDCl$_3$): δ8.23(2H, s, Ar—H), 8.15 (2H, s, Ar—H), 7.94–8.05(8H, m, Ar—H), 7.77(2H, dd, J=1.8, 8.4 Hz, Ar—H), 7.56–7.64(6H, m, Ar—H), 7.38–7.46 (4H, m, Ar—H)ppm.

Example 3

Preparation of (S)-1,1'-bi-3-phenyl-2-trifluoromethanesulfonyloxy naphthyl (4)

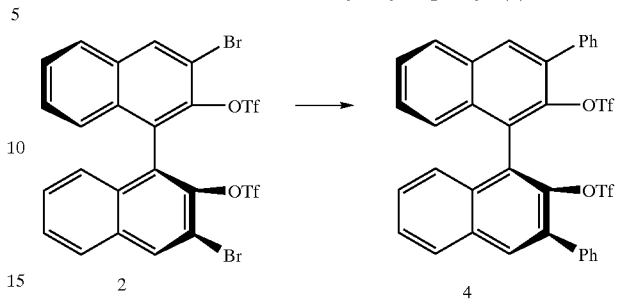

A mixture of (S)-1,1'-bi-3-bromo-2-trifluoromethaneulfonyloxy naphthyl (2) (3.54 g, 5.0 mmol), phenylboronic acid (PhB(OH)$_2$; 1.83 g 15 mmol), palladium acetate [Pd(OAc)$_2$; 57.9 mg, 5 mol %], triphenylphosphine (0.294 g, 22 mol %), potassium phosphate·hydrate (4.29 g, 15 mmol) and THF (25 mL) was stirred and heated at 65° C. for 10 hours. Then, the reaction mixture was poured into a saturated NH$_4$Cl aqueous solution. The palladium catalyst was filtered off, and the filtrate was extracted with ether. The ether extract was dried over Na$_2$SO$_4$, and then concentrated under vacuum. The residue was subjected to a silica gel chromatography, and elution with ether—dichloromethane—hexane (1:2:60) gave (S)-1,1'-bi-3-phenyl-2-trifluoromethanesulfonyloxynaphthyl (4) (2.99 g, 4.25 mmol) in 85% yield.

300 MHz $^1$H-NMR(CDCl$_3$): δ8.12(2H, s, Ar—H), 7.99 (2H, d, J=8.1 Hz, Ar—H), 7.34–7.66(16H, m, Ar—H) ppm.

Example 4

Preparation of (S)-1,1'-bi-2-methyl-3-(β-naphthyl) naphthyl (5)

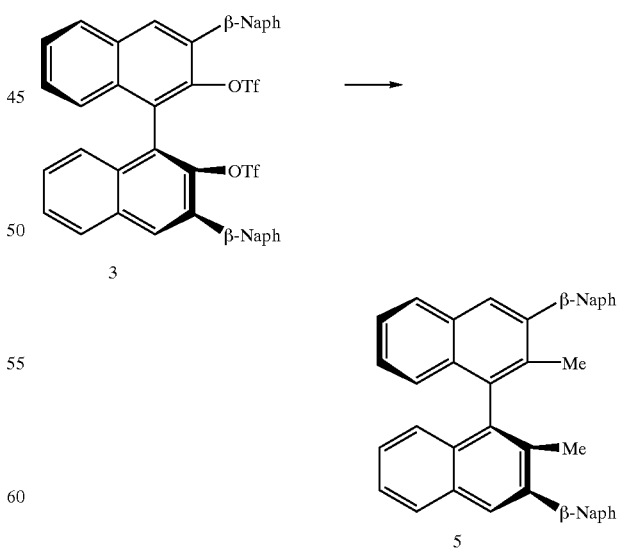

Under argon atmosphere, a solution of MeMgI in ether (1.0; 14 mL, 14 mmol) was added dropwise to a mixture of (S)-1,1'-bi-3-(β-naphthyl)-2-trifluoromethanesulfonyloxy naphthyl (3) (1.73 g, 2.4 mmol), bis(triphenylphosphine) nickel chloride [NiCl$_2$(PPh$_3$)$_2$; 78.5 mg, 5 mol %] and ether (4 mL) at 0° C. The reaction mixture was stirred and heated at reflux for 30 hours, and poured into a saturated NH$_4$Cl aqueous solution. The mixture was extracted with ether, and the ether extract was filtered to remove the nickel catalyst. The filtrate was washed with brine, dried over Na$_2$SO$_4$, and concentrated under vacuum. The residue was chromatographed over silica gel, and elution with ether—hexane (1:100) gave (S)-1,1'-bi-2-methyl-3-(β-naphthyl)naphthyl (5) (0.793 g, 1.5 mmol) in 62% yield.

300 MHz $^1$H-NMR(CDCl$_3$): δ7.91–7.98(10H, m, Ar—H), 7.63(2H, dd, J=1.8, 8.7 Hz, Ar—H), 7.52–7.55(4H, m, Ar—H), 7.46(2H, ddd, J=1.2, 6.9, 8.1 Hz, Ar—H, 7.30(2H, ddd, J=1.2, 6.9, 8.1 Hz, Ar—H), 7.20(2H, d, J=8.7 Hz, Ar—H), 2.03(6H, s, CH$_3$)ppm.

Example 5

Preparation of (S)-1,1'-bi-2-methyl-3-phenylnaphthyl (6)

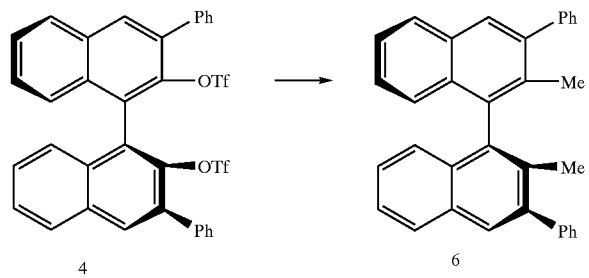

Under argon atmosphere, a solution of MeMgI in ether (1.0M; 15 mL, 15 mmol) was added dropwise to a mixture of (S)-1,1'-bi-3-phenyl-2-trifluoromethanesulfonyloxy naphthyl (4) (1.72 g, 2.5 mmol), bis(triphenylphosphine) nickel chloride [NiCl$_2$(PPh$_3$)$_2$; 80.1 mg, 5 mol %] and ether (5 mL) at 0° C. The reaction mixture was stirred and heated at reflux for 30 hours, and poured into a saturated NH$_4$Cl aqueous solution. The mixture was extracted with ether, and the extract was filtrated to remove the nickel catalyst. The filtrate was washed with brine, dried over Na$_2$SO$_4$, and concentrated under vacuum. The residue was chromatographed over silica gel, and elution with ether—hexane (1:100) gave (S)-1,1'-bi-2-methyl-3-phenylnaphthyl (6) (0.925 g, 2.1 mmol) in 87% yield.

300 MHz $^1$H-NMR(CDCl$_3$): δ7.85–7.91(4H, m, Ar—H), 7.36–7.51 (12H, m, Ar—H), 7.25(2H, ddd, J=1.2, 8.4, 9.9 Hz, Ar—H), 7.12(2H, d, J=8.4 Hz, Ar—H), 1.95(6H, s, CH$_3$) ppm.

Example 6

Preparation of (S)-1,1'-bi-2-(bromomethyl)-3-(β-naphthyl)naphthyl (7)

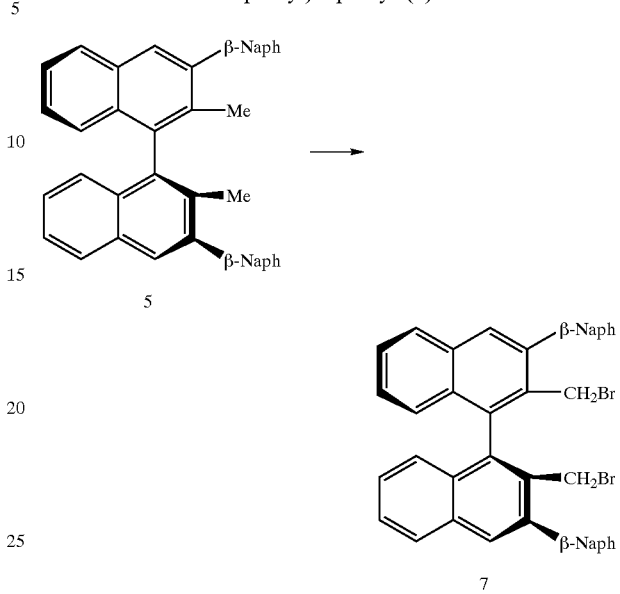

A mixture of (S)-1,1'-bi-2-methyl-3-(β-naphthyl)naphyl (5) (0.793 g, 1.5 mmol), N-bromosuccinimide (0.654 g, 3.6 mmol), benzoyl peroxide (96.9 mg, 0.3 mmol) and cyclohexane (6 mL) was stirred and heated st reflux for 3 hours, during which benzoyl peroxide (96.9 mg, 0.3 mmol) was added twice at one-hour interval. The reaction mixture was poured into a saturated sodium sulfite aqueous solution, and the mixture was extracted with ether. The ether extract was washed with brine, dried over Na$_2$SO$_4$, and then concentrated under vacuum. The residue was chromatographed over silica gel. Elution with ether—hexane (1:100) gave (S)-1,1'-bi-(bromomethyl)-3-phenylnaphthyl (7) (0.982 g 1.4 mmol) in 95% yield.

300 MHz $^1$H-NMR(CDCl$_3$): δ8.12(2H, d, J=1.5 Hz, Ar—H), 7.93–8.01(10H, m, Ar—H), 7.77(2H, dd, J=1.8, 8.4 Hz, Ar—H), 7.52–7.57(6H, m, Ar—H), 7.34(2H, ddd, J=1.5, 6.9, 8.1 Hz, Ar—H), 7.24(2H, d, J=9.0 Hz, Ar—H), 4.36 (4H, s, CH$_2$Br) ppm.

Example 7

Preparation of (S)-1,1'-bi-2-(bromomethyl)-3-phenylnaphthyl (8)

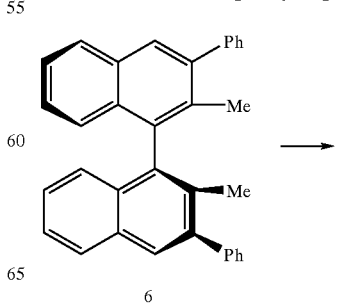

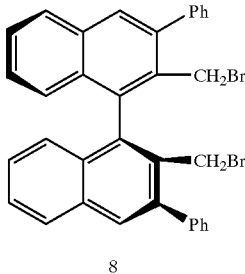

8

A mixture of (S)-1,1'-bi-2-methyl-3-phenylnaphthyl (6) (0.405 g, 0.93 mmol), N-bromosuccinimde (0.40 g, 2.2 mmol), benzoyl peroxide (65.0 mg, 0.2 mmol) and cyclohexane (3 mL) was stirred and heated at reflux for an hour. The reaction mixture was poured into a saturated sodium sulfite aqueous solution, and extracted with ether. The ether extract was washed with brine, dried over $Na_2SO_4$, and concentrated under vacuum. The residue was subjected to silica gel chromatography, and elution with ether—hexane (1:100) gave (S)-1,1'-bi-2-(bromomethyl)-3-phenylnaphthyl (8) (0.55 g, 0.93 mmol) quantitatively.

300 MHz $^1$H-NMR(CDCl$_3$): δ7.92(4H, t, J=8.1 Hz, Ar—H), 7.61–7.65(4H, m, Ar—H), 7.45–7.55(8H, m, Ar—H), 7.30(2H, ddd, J=1.5, 6.9, 8.4 Hz, Ar—H), 7.18)2H, d, J=7.2 Hz, Ar—H), 4.29(4H, s, CH$_2$Br) ppm.

Example 8

Preparation of spiro bi[(S)-1,1'-binaphthyl-2,2'-dimethylammonium]bromide (11)

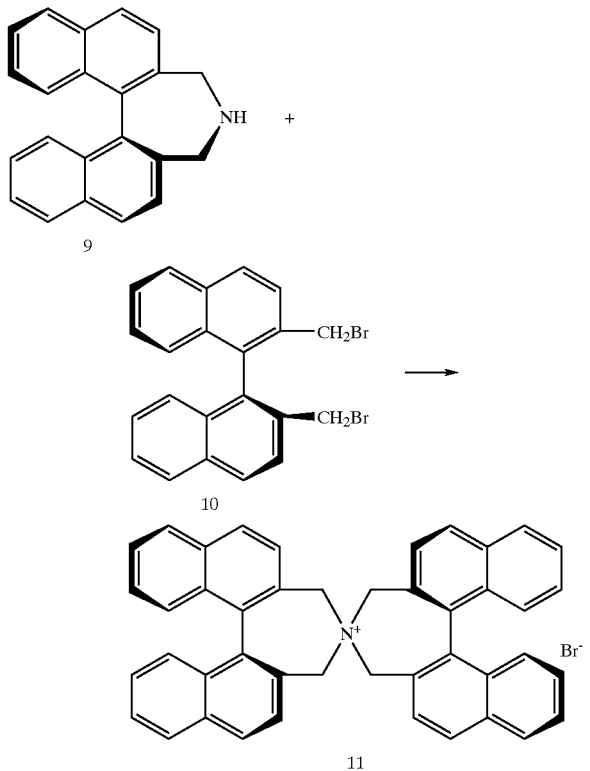

Potassium carbonate (0.417 g, 3.0 mmol) was added to a solution of (S)-3,5-dihydro-4H-[2,1-c:1',2'-e]azepine (9) (0.295 g, 1.0 mmol) in methanol (3 mL), and the mixture was stirred at room temperature for 30 minutes. Then, (S)-1,1'-bi-2-(bromomethyl) naphthyl (10) (0.44 g, 1.0 mmol) was added. The reaction mixture was stirred under heating at reflux for 8 hours, and poured into water. The mixture was extracted with dichloromethane. The dichloromethane extract was dried over $Na_2SO_4$, and concentrated under vacuum. The residue was subjected to silica gel chromatography, and elution with methanol—dichloromethane (1:30) gave compound (11) (0.465 g, 1.71 mmol) in 71% yield.

300 MHz $^1$H-NMR(CDCl$_3$): δ8.38(4H, d, J=8.1 Hz, Ar—H), 8.17(4H, d, J=6.6 Hz, Ar—H), 8.11(4H, d, J=6.6 Hz, Ar—H). 7.64(4H, ddd, J=1.4, 6.6, 8.1 Hz, Ar—H), 7.26–7.44(8H, m, Ar—H), 4.52(4H, d, J=13.2 Hz, ArCH$_2$), 3.92(4H, d, J=13.2 Hz, ArCH$_2$) ppm; IR(KBr): ν3647, 3400, 3053, 2361, 1624, 1595, 1508, 1458, 1346, 1030, 862, 822, 756 cm$^{-1}$; MS: 574(M$^+$)(100%).

Example 9

Preparation of [(S)-3,3'-diphenyl-1,1'-binaphenyl-2,2'-dimethyl ammonium] spiro [(S)-1,1'-binaphthyl-2,2'-dimethylamine]bromide (12)

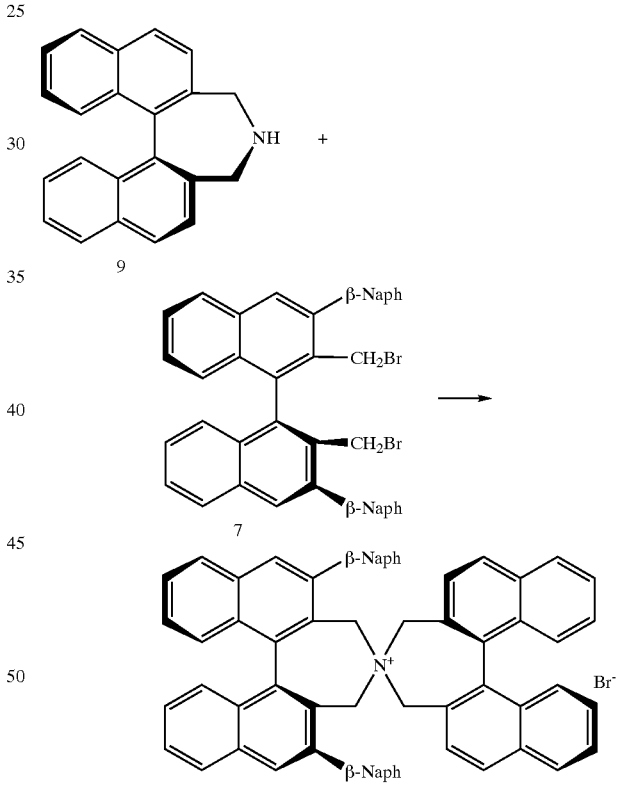

Potassium carbonate (0.208 g, 1.5 mmol) was added to a solution of (S)-3,5-dihydro-4H-[2,1-c:1',2'-e]azepine (9) (0.148 g, 0.5 mmol) in methanol (3 mL), and the mixture was stirred at room temperature for 30 minutes. Then, (S)-1,1'-bi-2-(bromomethyl)-3-(β-naphthyl)naphthyl (7) (0.346 g, 0.5 mmol) was added. The reaction mixture was stirred under heating at reflux for 8 hours, and poured into water. The mixture was extracted with dichloromethane. The dichloromethane extract was dried over $Na_2SO_4$, and concentrated under vacuum. The residue was subjected to silica gel chromatography, and elution with methanol—dichloromethane (1:30) gave compound (12) (0.162 g, 0.17 mmol) in 36% yield.

300 MHz $^1$H-NMR(CDCl$_3$): δ8.49(2H, s, Ar—H), 8.16 (2H, d, J=8.4 Hz, Ar—H), 8.14(2H, br, Ar—H), 7.79(2H, br, β-Np), 7.67(2H, t, J=6.9 Hz, Ar—H), 7.31–7.39(4H, m, Ar—H), 7.20(2H, d, J=7.5 Hz, Ar—H), 7.08(2H, t, J=6.8 Hz, Ar—H), 6.94(2H, d, J=9.0 Hz, Ar—H), 7.0–8.6(12H, br, β-Np), 5.05(2H, br, ArCH$_2$), 4.50(2H, d, J=13.8 Hz, ArCH$_2$), 4.22(2H, d, J=12.9 Hz, ArCH$_2$), 3.66(2H, d, J=12.9 Hz, ArCH$_2$), ppm; IR(KBr): ν3852, 3649, 3367, 3051, 1653, 1558, 1506, 1456, 1361, 853, 833, 749 cm$^{-1}$.

Example 10

Preparation of [(S)-3,3'-di(62 -naphthyl)-1,1'-binaphthyl-2,2'-dimethylammonium]spiro[(S)-1,1'-binaphthyl-2,2'-dimethylamine]bromide (13)

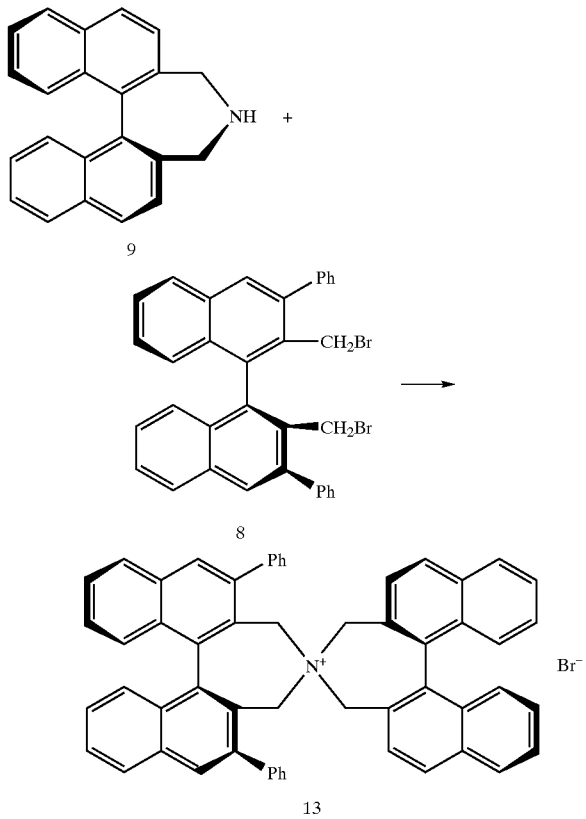

Potassium carbonate (83.0 mg, 0.6 mmol was added to a solution of (S)-3,5-dihydro-4H-[2,1-c:1',2'-e]azepine (9) (89 mg, 0.3 mmol) in methanol (3 mL), and the mixture was stirred at room temperature for 30 minutes. Then, (S)-1,1'-bi-2-(bromomethyl)-3-phenylnaphthyl (8) (0.178 g, 0.3 mmol) was added. The reaction mixture was stirred under heating at reflux for 8 hours, and poured into water. The mixture was extracted with dichloromethane. The dichloromethane extract was dried over Na$_2$SO$_4$, and then concentrated under vacuum. The residue was subjected to silica gel chromatography, and elution with methanol—dichloromethane (1:30) gave compound (13) (0.196 g, 0.24 mmol) in 81% yield.

300 MHz $^1$H-NMR (CDCl$_3$): δ8.34(2H, s), 8.11(2H, d, J=8.1 Hz, Ar—H), 7.84(2H, d, J=8.1 Hz, Ar—H), 7.74(2H, br, Ph), 7.63(2H, ddd, J=1.1, 7.2, 8.0 Hz, Ar—H), 7.49(2H, ddd, J=1.1, 7.2, 8.0 Hz, Ar—H), 7.31–7.36(4H, m, Ar—H), 7.09–7.22(6H, m, Ar—H), 7.2–8.2(8H, br, Ph), 6.32(2H, d, J=8.4 Hz, Ar—H), 5.01(2H, d, J=13.7 Hz, ArCH$_2$), 4.40(2H, d, J=13.2 Hz, ArCH$_2$), 4.24(2H, d, J=13.7 Hz, ArCH$_2$), 3.71(2H, d, J=13.2 Hz, ArCH$_2$) ppm; IR(KBr): ν3649, 3367, 3053, 1653, 1558, 1491, 1456, 847, 812, 752, 708 cm$^{-1}$.

Example 11

Preparation of (S)-N,N-di(62-naphthyl)-3,5-dihydro-4H-[2,1-c:1',2'-e]azepinium bromide (14a)

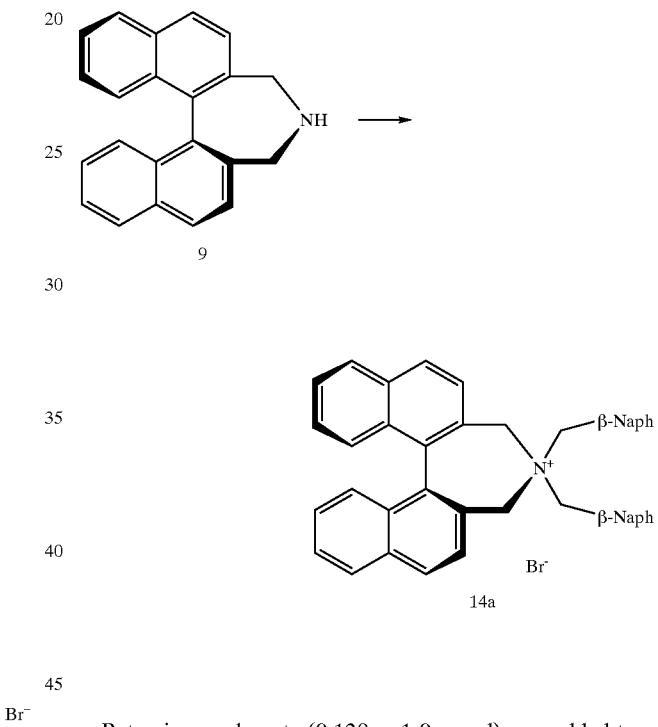

Potassium carbonate (0.139 g, 1.0 mmol) was added to a solution of (S)-3,5-dihydro-4H-[2,1-c:1',2'-e]azepine (9) (0.148 mg, 0.5 mmol) in methanol (3 mL), and the mixture was stirred at room temperature for 30 minutes. Then, 2-(bromomethyl) naphthalene (0.276 g, 1.2 mmol) was added. The reaction mixture was stirred under heating at reflux for 3 hours, and poured into water. The mixture was extracted with dichloromethane. The dichloromethane extract was dried over Na$_2$SO$_4$ and concentrated under vacuum. The residue was subjected to silica gel chromatography, and elution with methanol-dichloromethane (1:30) gave compound (14a) (0.220 g, 0.34 mmol) in 68% yield.

300 MHz $^1$H-NMR(CDCl$_3$): δ8.05 (2H, s, Ar—H), 7.81–7.86(6H, m, Ar—H), 7.75(2H, d, J=8.7 Hz, Ar—H), 7.49–7.66(10H, m, Ar—H), 7.23–7.31(6H, m, Ar—H), 6.07 (2H, d, J=13.2 Hz, ArCH$_2$), 5.38(2H, d, J=13.2 Hz, ArCH$_2$), 4.85(2H, d, J=12.9 Hz, ArCH$_2$), 4.42(2H, d, J=12.9 Hz, ArCH$_2$) ppm.

Example 12

Preparation of (S)-N,N-di(α-naphthyl)-3,5-dihydro-4H-[2,1-c:1',2'-e]azepinium bromide (14b)

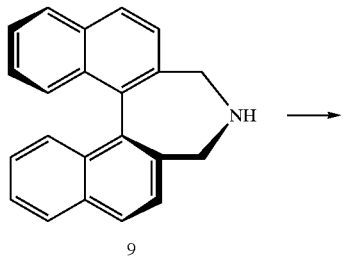

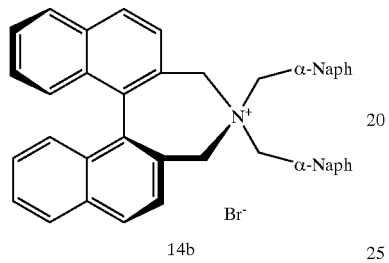

According to the method described in Example 11, compound (14b) was obtained from (S)-3,5-dihydro-4H-[2,1-c:1',2'-e]azepine and 1-(bromomethyl) naphthalene in 24% yield.

300 MHz $^1$H-NMR(CDCl$_3$): δ7.96(4H, dd, J=8.1, 18.0 Hz, Ar—H), 7.89(4H, d, J=8.4 Hz, Ar—H), 7.74–7.62(6H, m, Ar—H), 7.56–7.46(4H, m, Ar—H), 7.39–7.18(6H, m, Ar—H), 6.89(2H, d, J=8.1 Hz, Ar—H), 6.39(2H, d, J=13.8 Hz, ArCH$_2$), 5.51(2H, d, J=13.8 Hz, ArCH$_2$), 5.30(2H, d, J=13.2 Hz, ArCH$_2$), 4.50 (2H, d, J=13.2 Hz, ArCH$_2$) ppm.

Example 13

Preparation of (S)-N,N-dibenzyl-3,5-dihydro-4H-[2,1-c;1',2'e] azepinium bromide (15)

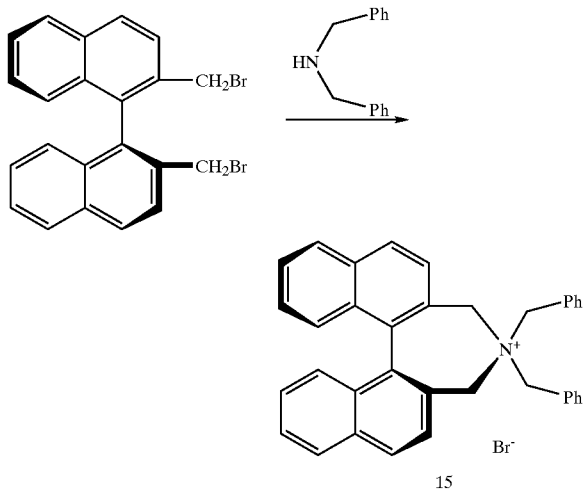

Potassium carbonate (55 mg, 0.4 mmol) was added to a solution of dibenzylamine (39 mL, 0.2 mmol) in methanol (3 mL), and the mixture was stirred at room temperature for 30 minutes. Then, (S)-1,1'-bi-2-(bromomethyl) naphthyl (88 mg, 0.2 mmol) was added. The mixture was stirred under heating at reflux for 4 hours, and poured into water. The mixture was extracted with dichloromethane. The dichloromethane extract was dried over Na$_2$SO$_4$, and concentrated under vacuum. The residue was chromatographed over silica gel, and elution with methanol—dichloromethane (1:30) gave compound (15) (55 mg, 0.1 mmol) in 50% yield.

300 MHz $^1$H-NMR(CDCl$_3$): δ7.95(2H, d, J=8.1 Hz, Ar—H), 7.87(2H, d, J=8.7 Hz, Ar—H), 7.54–7.65(8H, m, Ar—H), 7.27–7.43(10H, m, Ar—H, 5.76(2H, d, J=13.2 Hz, ArCH$_2$), 5.20(2H, d, J=12.9 Hz, ArCH$_2$), 4.69(2H, d, J=13.2 Hz, ArCH$_2$), 4.30(2H, d, J=12.9 Hz, ArCH$_2$) ppm.

Example 14

Preparation of (S)-phenylalanine tert-butylester benzophenone Schiff base (17)

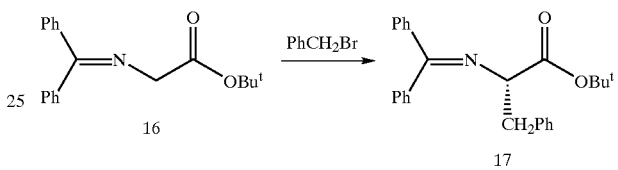

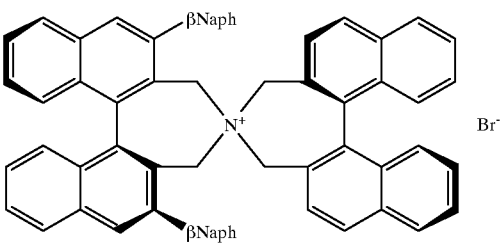

Benzyl bromide (72.1 μL, 0.6 mmol) was added dropwise to the mixture of glycine tert-butylester benzophenone Schiff base (16) (148 mg, (0.5 mmol), phase-transfer catalyst (12) (45 mg, 0.005 mmol), toluene (3.25 mL) and 50% potassium hydroxide aqueous solution (1.05 mL) at 0° C. The mixture was stirred at 0° C. for 30 minutes and poured into water. The mixture was extracted with ether. Then, the ether extract was washed with brine, dried over Na$_2$SO$_4$, and concentrated under vacuum. The oily residue was subjected to silica gel chromatography, and elution with ether—hexane (1:10) gave (S)-phenylalanine tert-butylester benzophenone Schiff base (17) (183 mg, 0.475 mmol) in 95% yield, which showed optical purity of 96% e.e. as demonstrated by HPLC analysis; DAICEI CHIRAL OD; hexane:2-propanol (100:1), 0.5 mL/min.; (R) form:14.8 min., (S) form:28.2 min.

Examples 15–23

Other examples of the stereoselective alkylation of glycine tert-butylester benzophenone Schiff base (16) using phase-transfer catalyst (12) in the same manner as in Example 14, are listed in Table 1.

TABLE 1

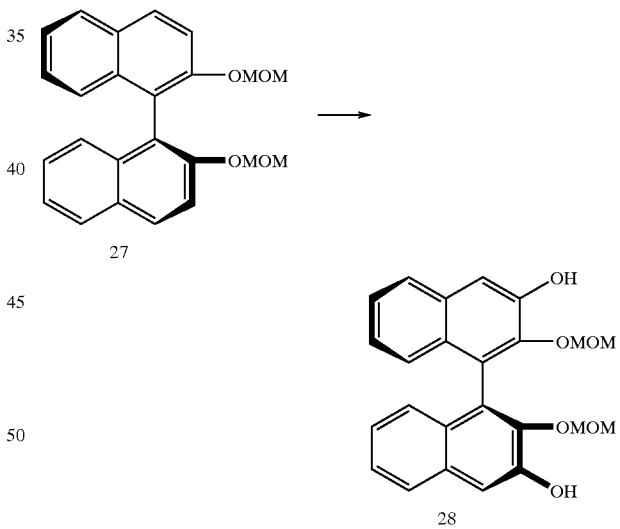

| Example | RX | Reaction °C.; hr | yield (%) | product | optical purity (% ee) |
|---|---|---|---|---|---|
| 15 | CH₃I | 0; 8 | 64 | 18 | 90 |
| 16 | CH₃CH₂I | 0; 10 | 41 | 19 | 95 |
| 17 | allyl Br | 0; 1 | 84 | 20 | 94 |
| 18 | methallyl Br | 0; 1 | 82 | 21 | 93 |
| 19 | propargyl Br | 0; 1 | 90 | 22 | 95 |
| 20 | 4-Me-benzyl Br | 0; 1 | 80 | 23 | 96 |
| 21 | 3-MeO-benzyl Br | 0; 0.5 | 58 | 24 | 91 |
| 22 | 4-F-benzyl Br | 0; 1 | 81 | 25 | 96 |
| 23 | 2-naphthylmethyl Br | 0; 1 | 76 | 26 | 90 |

As shown in Table 1, when the present optically active quaternary ammonium salts with axial chirality are used as phase-transfer catalysts, it is found that glycine tert-butylester benzophenone Schiff base can be stereoselectively alkylated in high optical purity.

Examples 24–26

Other examples of the stereoselective alkylation glycine tert-butylester benzophenone Schiff base (16) with benzyl bromide using phase-transfer catalyst (14a), (14b) or (15), are listed in Table 2.

TABLE 2

14a Ar = β–Naph
b Ar = α–Naph
15 Ar = Ph

| Example | Phase-transfer catalyst | Reaction °C.; hr | yield (%) | product | optical purity(% ee) |
|---|---|---|---|---|---|
| 24 | 14a | 0; 6 | 44 | 17 | 17 |
| 25 | 14b | 0; 6 | 46 | 17 | 28 |
| 26 | 15 | 0; 6 | 34 | 17 | 21 |

Example 27

Preparation of (S)-1,1'-bi-3-hydroxy-2-methoxymethoxynaphthyl (28)

Under argon atmosphere, a solution of n-butyllithium in hexane (1.60M, 30.0 ml, 48 mmol) was added dropwise to a solution of compound (27) (7.50 g, 20 mmol; prepared by the method of Katsuki et al., *Chem. Lett.* 1995, 1113) in ether (120 ml) at room temperature. After stirring for 4 hours, the reaction mixture was cooled to −78° C., and THF (150 ml) was added. After trimethoxyborane (6.73 ml, 60 mmol) was added dropwise, the mixture was allowed to warm to room temperature, and then stirred for 10 hours. The reaction mixture was concentrated under vacuum with a rotary evaporator, and benzene (100 ml) was added. The mixture was cooled to 0° C., and then hydrogen peroxide solution (30%, 10 ml) was added dropwise. The reaction mixture was stirred and heated at reflux for 2 hours, and poured into a saturated $Na_2SO_3$ aqueous solution. The mixture was extracted with ether. The ether extract was washed with brine, dried over $Na_2SO_4$, and concentrated under vacuum. The residue was subjected to silica gel chromatography, and elution with ethyl acetate - hexane (1:2) gave compound (28) (6.05 g, 15 mmol) in 75% yield.

300 MHz $^1$H-NMR(CDCl$_3$): δ7.78(2H, d, J=8.4 Hz, Ar-H), 7.51(2H, s, Ar-H), 7.45(2H, s, ArOH), 7.34(2H, ddd, J=1.2, 6.9, 7.8 Hz, Ar-H), 7.12(2H, ddd, J=1.2, 6.9, 7.8 Hz, Ar-H), 7.04(2H, d, J=8.4 Hz, Ar-H), 4.72(2H, d, J=6.3 Hz, ArOCH$_2$), 4.64(2H, d, J=6.3 Hz, ArOCH$_2$), 3.40(6H, s, OCH$_3$) ppm.

Example 28

Preparation of (S)-1,1'-bi-3-methoxy-2-methoxymethoxynaphthyl (29)

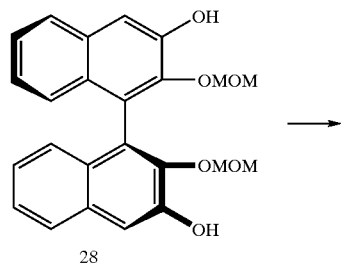

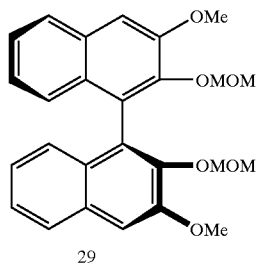

A mixture of compound (28) (6.05 g, 15 mmol), potassium carbonate (6.25 g, 45 mmol), methyl iodide (4.86 ml, 75 mmol) and acetone (200 ml) was stirred under heating at reflux for 6 hours. Then, the reaction mixture was poured into water, and the mixture was extracted with ether. The ether extract was washed with brine, dried over $Na_2SO_4$, and then concentrated under vacuum. The residue was subjected to silica gel chromatography, and elution with ethyl acetate - hexane (1:3) gave compound (29) (5.60 g, 13 mmol) in 86% yield.

300 MHz $^1$H-NMR(CDCl$_3$): δ7.76(2H, d, J=8.1 Hz, Ar-H), 7.36(2H, ddd, J=1.2, 6.0, 8.1 Hz, Ar-H), 7.30(2H, s, Ar-H), 7.10–7.18(4H, m, Ar-H), 4.97(2H, d, J=5.7 Hz, ArOCH$_2$), 4.83(2H, d, J=5.7 Hz, ArOCH$_2$), 4.03(6H, s, ArOCH$_3$), 2.57(6H, s, OCH$_3$) ppm.

Example 29

Preparation of (S)-1,1'-bi-2-hydroxy-3-methoxynaphthyl (30)

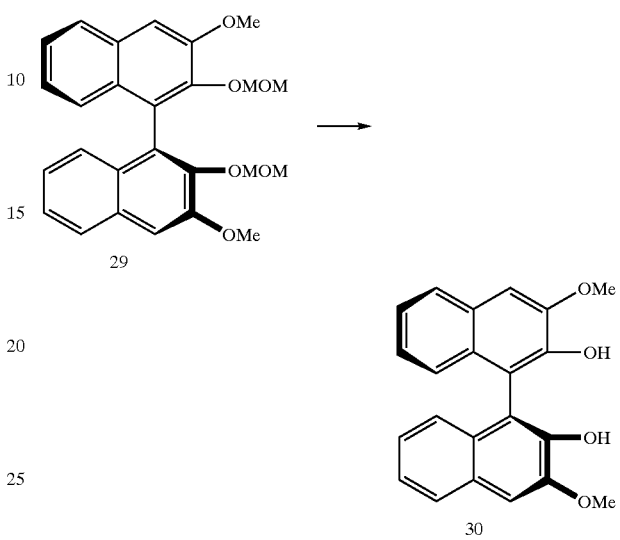

A mixture of compound (29) (5.60 g, 13 mmol), 1,4-dioxane (40 ml) and concentrated hydrochloric acid (1 ml) was stirred and heated at 50° C. for 4 hours. Then, the reaction mixture was poured into water, and the mixture was extracted with ether. The ether extract was washed with water and brine, dried over $Na_2SO_4$, and concentrated under vacuum. The residue was chromatographed over silica gel. Elution with ethyl acetate - hexane (1:1) gave compound (30) (4.50 g, 13 mmol) in a quantitative yield.

300 MHz $^1$H-NMR(CDCl$_3$): δ7.78(2H, d, J=8.1 Hz, Ar-H), 7.32(2H, ddd, J=2.4, 5.7, 8.4 Hz, Ar-H), 7.30(2H, s, Ar-H), 7.12–7.19(4H, m, Ar-H), 5.89(2H, s, ArOH), 4.10 (6H, s, ArOCH$_3$), ppm.

Example 30

Preparation of (S)-1,1'-bi-3-methoxy-2-trifluoromethanesulfonyloxy naphthyl (31)

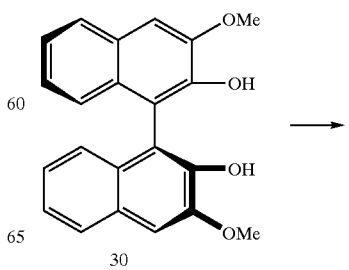

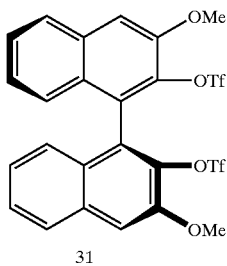

31

Under argon atmosphere, triethylamine (5.52 ml, 39 mmol) was added to a solution of compound (30) (4.50 g, 13 mmol) in dichloromethane (50 ml) at room temperature. Then, the solution was cooled to −78° C. After trifluoromethanesulfonic anhydrade (5.17 ml, 31 mmol) was added dropwise, the reaction mixture was aallowed to warm to room temperature and stirred for 2 hours. The reaction mixture was poured into a saturated NH$_4$Cl aqueous solution, and the mixture was extracted with dichloromethane. The dichrometaner extract was dried over Na$_2$SO$_4$, and concentrated under vacuum. The residue was subject to silica gel chromatography, and elution with dichloromethane - hexane (1:3) gave compound (31) (7.72 g, 13 mmol) in a quantitative yield.

300 MHz $^1$H-NMR(CDCl$_3$): δ7.87(2H, d, J=8.4 Hz, Ar-H), 7.52(2H, ddd, J=1.2, 6.9, 8.4 Hz, Ar-H), 7.49(2H, s, Ar-H), 7.24(2H, ddd, J=1.2, 6.9, 7.8 Hz, Ar-H), 7.14(2H, d, J=7.8 Hz, Ar-H), 4.12 (6H, s, ArOCH$_3$), ppm.

Example 31

Preparation of (S)-1,1'-bi-3-methoxy-2-methylnaphthyl (32)

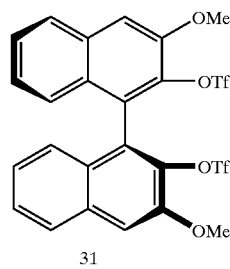

31

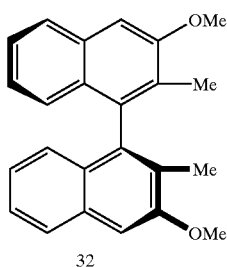

32

Under argon atmosphere, a solution of MeMgI in ether (1.0M, 75 ml, 75 mmol) was added dropwise to a mixture of compound (31) (7.72 g, 13 mmol), [1,3-bis(diphenyl phosphino)propane]nickel chloride [NiCl$_2$(dppp), 342 mg, 5 mol %], and ether (20 ml) at 0° C. The reaction mixture was stirred at room temperature for 30 hours, and then poured into saturated NH$_4$Cl aqueous solution. The nickel catalyst was filtered off, and the filtrate was extracted with ether. The ether extract was washed with brine, dried over Na$_2$SO$_4$ and concentrated under vacuum. The residue was chromatographed over silica gel. Elution with ether - hexane (1:10) gave compound (32) (3.40 g, 9.9 mmol) in 76% yield.

300 MHz $^1$H-NMR(CDCl$_3$): δ7.80(2H, d, J=8.1 Hz, Ar-H), 7.36(2H, ddd, J=1.2, 6.9, 8.1 Hz, Ar-H), 7.26(2H, s, Ar-H), 7.06(2H, ddd, J=1.2, 6.9, 8.1 Hz, Ar-H), 6.96(2H, d, J=8.1 Hz, Ar-H), 4.03(6H, s, ArOCH$_3$), 1.92(6H, s, ArCH$_3$) ppm.

Example 32

Preparation of (S)-1,1'-bi-3-hydroxy-2-methylnaphthyl (33)

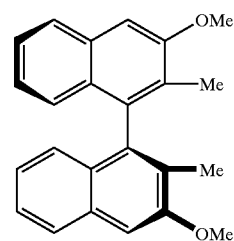

32

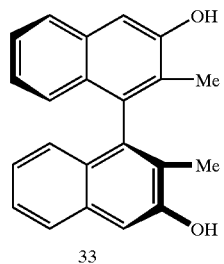

33

Under argon atmosphere, boron tribromide (2.27 ml, 24 mmol) was added dropwise to a solution of compound (32) (3.40 g, 9.9 mmol) in dichloromethane (40 ml) at 0° C. The reaction mixture was allowed to warm to room temperature and stirred for 2 hours. The mixture was then cooled to 0° C. again, and water was added dropwise. The mixture was extracted with dichloromethane. The dichloromethane extract was washed with brine, dried over Na$_2$SO$_4$, and concentrated under vacuum. The residue was subjected to silica gel chromatography, and elution with ethyl acetate - hexane (1:1) gave compound (33)(3.13 g, 9.9 mmol) in a quantitative yield.

300 MHz $^1$H-NMR(CDCl$_3$): δ7.74(2H, d, J=8.4 Hz, Ar-H), 7.36(2H, ddd,J=1.5, 6.9, 8.1 Hz, Ar-H), 7.27(2H, s, Ar-H), 7.07(2H, ddd, J=1.5, 6.9, 8.4 Hz, Ar-H), 6.96(2H, d, J=8.1 Hz, Ar-H), 5.14(6H, s, ArOH), 1.97(6H, s, ArCH$_3$) ppm.

Example 33

Preparation of (S)-1,1'-bi-2-methyl-3-trifluoromethanesulfonyloxy-naphthyl (34)

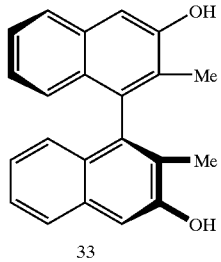

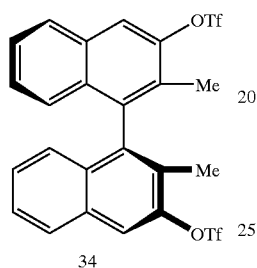

Under argon atmosphere, triethylamine (4.20 ml, 30 mmol) was added to a solution of compound (33) (3.13 g, 9.9 mmol) in dichloromethane (30 ml) at room temperature. Then, the solution was cooled to −78° C. After trifluoromethanesulfonic anhydrade (4.04 ml, 24 mmol) was added dropwise, the reaction mixture was allowed to warm to room temperature and stirred for 2 hours. The reaction mixture was poured into a saturated NH$_4$Cl aqueous solution, and the mixture was extracted with dichloromethane. The dichloromethane extract was dried over Na$_2$SO$_4$, and concentrated under vacuum. The residue was subjected to silica gel chromatography, and elution with dichloromethane - hexane (1:5) gave compound (34) (5.44 g, 9.4 mmol) in 95% yield.

300 MHz $^1$H-NMR(CDCl$_3$): δ7.96(2H, d, J=8.4 Hz, Ar-H), 7.94(2H, s, Ar-H), 7.54(2H, ddd, J=1.2, 6.9, 8.4 Hz, Ar-H), 7.34(2H, ddd, J=1.2, 6.9, 8.4 Hz, Ar-H), 6.99(2H, d, J=8.4 Hz, Ar-H), 2.04(6H, s, ArCH$_3$) ppm.

Example 34

Preparations of (S)-1,1'-2-methyl-3-(3",4", 5"-trifluorophenyl)naphthyl (35)

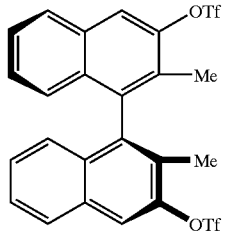

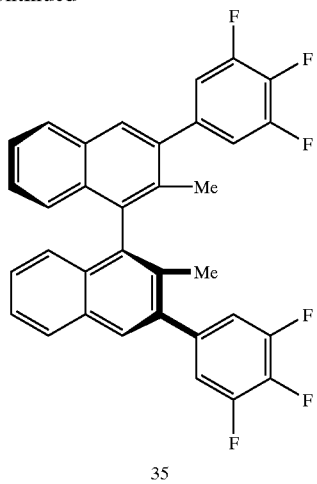

Under argon atmosphere, a mixture of compound (34) (289 mg, 0.50 mmol), 3,4,5-trifluorophenyl boronic acid (211 mg, 1.2 mmol), tetrakis(triphenylphosphine) palladium (28.9 mg, 5 mol %), potassium phosphate.hydrate (429 mg, 1.5 mmol) and dioxane (5 ml) was stirred and heated at 80° C. for 10 hours. Then, the reaction mixture was poured into brine. The palladium catalyst was filtered off and the filtrate was extracted with ether. The ether extract was dried over Na$_2$SO$_4$ and concentrated under vacuum. The residue was subject to silica gel chromatography, and elution with dichloromethane - hexane (1:20) gave compound (35) (253 mg, 0.47 mmol) in 94% yield.

300 MHz $^1$H-NMR(CDCl$_3$): δ7.91(2H, d, J=8.1 Hz, Ar-H), 7.82(2H, s, Ar-H), 7.47(2H, ddd, J=1.2, 6.9, 8.1 Hz, Ar-H), 7.29(2H, ddd, J=1.2, 6.9, 8.4 Hz, Ar-H), 7.05–7.14 (6H, m, Ar-H), 1.91(6H, s, ArCH$_3$) ppm.

Example 35

Preparation of (S)-1,1'-bis-2-bromomethyl-3-(3",4", 5"-trifluorophenyl)naphthyl (36)

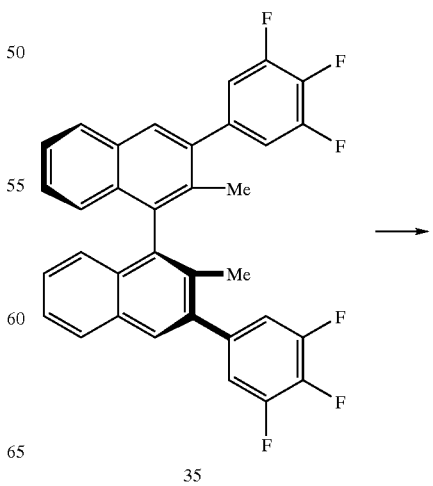

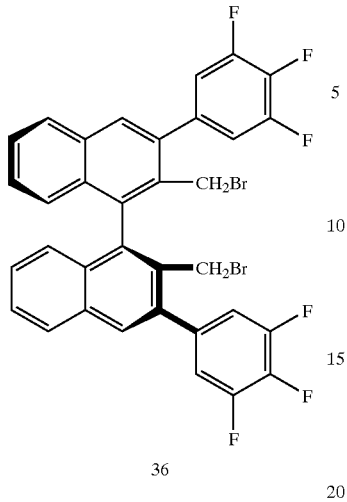

A mixture of compound (35) (253 mg, 0.47 mmol), 2,2'-azobis (isobutylonitrile) (7.9 mg, 10 mol %), N-bromosuccinimide (188 mg, 1.0 mmol) and benzene (4 ml) was stirred under heating at reflux for 2 hours. The reaction mixture was poured into water, and the mixture was extracted with ether. The ether extract was dried over $Na_2So_4$ and concentrated under vacuum. The residue was chromatographed over silica gel. Elution with ether - hexane (1:20) gave compound (36) (309 mg, 0.44 mmol) in 94% yield.

300 MHz $^1$H-NMR(CDCl$_3$): δ7.94(2H, d, J=8.1 Hz, Ar-H), 7.89(2H, s, Ar-H), 7.57(2H, ddd, J=1.2, 6.9, 8.1 Hz, Ar-H), 7.34(2H, ddd, J=1.2, 6.9, 8.1 Hz, Ar-H), 7.25–7.30 (4H, M, Ar-H), 7.13(2H, d, J=8.1 Hz, Ar-H), 4.19(4H, s, CH$_2$Br) ppm.

Example 36

Preparation of [(S)-3,3'-di(3",4",5"-trifluorophenyl)-1,1'-binaphthyl-2,2'-dimethylammonium]spiro[(S)-1,1'-binaphthyl-2,2'-dimethyl amine] bromide (38)

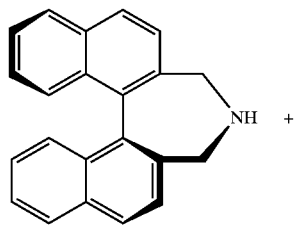

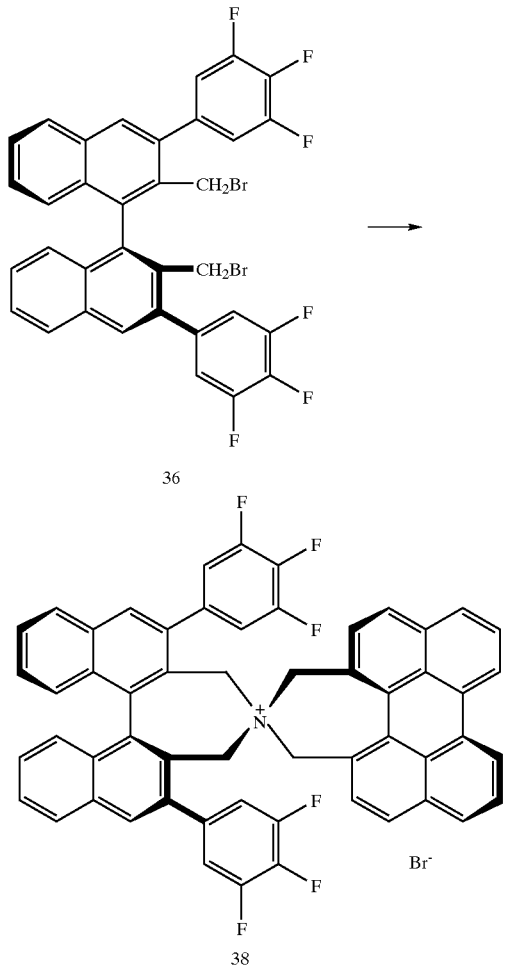

Potassium carbonate (62.5 mg, 0.45 mmol) was added to a solution of compound (37) (88.6 mg, 0.30 mmol) in acetonitrile (5 mL), and the mixture was stirred at room temperature for 30 minutes. Then, compound (36) (210 mg, 0.30 mmol) was added. The reaction mixture was stirred under heating at reflux for 3 hours, and then it was poured into water. The mixture was extracted with dichloromethane. The dichloromethane extract was dried over Na$_2$SO$_4$, and concentrated under vacuum. The residue was subjected to silica gel chromatography, and elution with methanol - dichloromethane (1:20) gave compound (38) (222 mg, 0.24 mmol) in 84% yield.

300 MHz $^1$H-NMR(CDCl$_3$): δ8.27(2H, s, Ar-H), 8.11(2H, d, J=8.4 Hz, Ar-H), 7.96(2H, d, J=8.7 Hz, Ar-H), 7.65(2H, t, J=7.8 Hz, Ar-H), 7.4–7.7(4H, br, Ar-H), 7.52–7.58(4H, m, Ar-H), 7.35(2H, t, J=7.8 Hz, Ar-H), 7.24–7.29(2H, m, Ar-H), 7.09–7.15(4H, m, Ar-H), 6.53(2H, d, J=8.4 Hz, Ar-H), 4.82(2H, d, J=14.1 Hz, ArCH$_2$), 4.62(2H, d, J=14.1 Hz, ArCH$_2$) 4.46(2H, d, J=13.2 Hz, ArCH$_2$(, 3.74(2H, d, J=13.2 Hz, ArCH$_2$) ppm. ; IR(KBr): v3647, 3360, 3055, 2981, 2954, 1614, 1526, 1450, 1360, 1242, 1047, 854, 750 cm$^{-1}$; [α]$_p^{23}$+33.6° (c0.2, CHCl$_3$), MS: m/z834(M$^+$) (100%), 281, 154, 136, 89.

Example 37

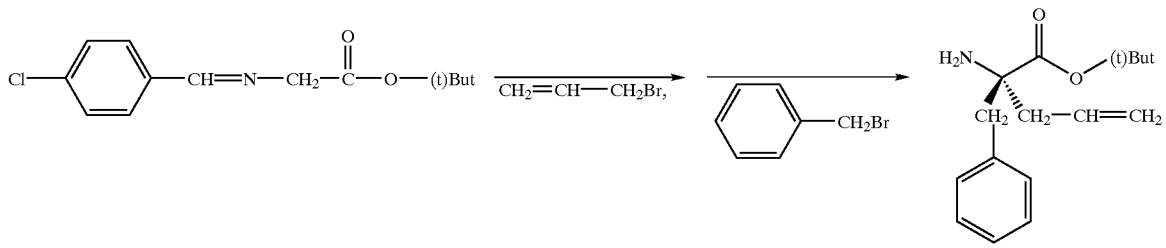

Cesium hydroxide.monohydrate (420 mg, 2.5 mmol) was added to a mixture of tert-butylglycinate P-chlorobenzaldehyde Schiff base (127 mg, 0.5 mmol), a chiral catalyst (compound (38) obtained from Example 36; 4.6 mg, 0.005 mmol), allyl bromide (43.3 μl, 0.5 mmol) and toluene (2 ml) at −10° C., and the mixture was stirred for 3.5 hours. After benzyl bromide (72.8 μl, 0.6 mmol) was added, the mixture was allowed to warm to 0° C. and stirred for 30 minutes. Water was added to the mixture, and the mixture was extracted with dichloromethane. After the solvent was removed off, the resultant residue was dissolved in tetrahydrofuran (5 ml). Then, 0.5M citric acid aqueous solution (5 ml) was added, and the mixture was stirred at room temperature for an hour. The water phase was separated, and washed with ether. Sodium bicarbonate was added to the water phase until it became alkaline. Then, the water phase was extracted with dichloromethane. The organic layer was dried over sodium sulfate and concentrated to obtain an oily product. This was subjected to silica gel chromatography (eluate/ethyl acetate ester: hexane=1:2) to give a colorless oily alkylated compound (tert-butylester of α-allyl phenylalanine): weight, 105 mg; yield. 80%; optical purity, 97% (R) [determined by chiral HPLC (DAICEL CHIRALPAK AD; hexane: isopropanol=100:1; flow rate 0.5 ml/min.); retention time: 14.9 minutes (R), 20.2 minutes (S)].

300 MHz $^1$H-NMR(CDCl$_3$): δ7.21–7.32(5H, m, Ph), 5.65–5.79(1H, m, CH=C), 5.13–5.22(2H, m, C=CH$_2$), 3.17 (1H, d, J=13.2 Hz, CHPh), 2.76(1H, d, J=13.2 Hz, CHPh), 2.69(1H, dd, J=6.3, 13.5 Hz, CHC=C), 2.28(1H, dd, J=8.6, 13.5 Hz, CHC=C), 1.60(2H, br s, NH$_2$), 1.46(9H, s, $^t$Bu).

Example 38

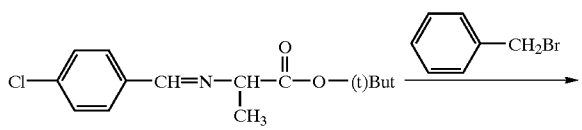

Cesium hydroxide.monohydrate (420 mg, 2.5 mmol) was added to a mixture of alanine tert-butylester p-chlorobenzyl Schiff base (134 mg, 0.5 mmol), a chiral catalyst (the compound (38) obtained from Example 36; 4.6 mg, 0.005 mmol), benzyl bromide (72.8 μl, 0.6 mmol) and toluene (2 ml) at 0° C., and the mixture was stirred for 30 minutes. After water was added, the mixture was extracted with dichloromethane. The solvent was removed, the residue was dissolved in tetrahydrofuran 5 ml). then, 0.5M citric acid aqueous solution (5 ml) was added to the solution, and the mixture was stirred at room temperature for an hour. The water phase was evaporated and washed with ether. Sodium bicarbonate was added to the water phase until it became alkaline. Then, the water phase was extracted with dichloromethane. The organic layer was dried over sodium sulfate, and concentrated to obtain an oily product. The oily product thus obtained was subjected to silica gel chromatography (eluate/ethyl acetate: hexane=2:1) to give a colorless oily alkylated compound (benzylalanine t-butylester); weight, 100 mg; yield, 85%; optical purity, 98% (R) [determined by chiral HPLC (DAICEL CHIRALPAK AD; hexane: isopropanol=30:1, flow rate 0.5 ml/min.); retention time:12.9 minutes (R), 20.5 minutes (S)].

300 MHz $^1$H-NMR(CDCl$_3$): δ7.20–7.30(5H, m, Ph), 3.12 (1H, d, J=13.2 Hz, CHPh), 2.78(1H, d, J=13.2 Hz, CHPh), 1.64(2H, s, NH$_2$), 1.46(9H, s, $^t$Bu), 1.35(3H, s, CH$_3$).

Examples 39–42

The following alkylated products were synthesized in the same manner as in Example 38.

| Example | Starting Compound | alkylating agent | Reaction ° C.; hr | yield (%) | optical purity(% ee) |
|---------|-------------------|------------------|-------------------|-----------|----------------------|
| 39 | Same as Example 38 | ⟋⟍Br | 0; 0.5 | 73 | 98(R) |

-continued

| Example | Starting Compound | alkylating agent | Reaction °C.; hr | yield (%) | optical purity(% ee) |
|---|---|---|---|---|---|
| 40 | Same as Example 38 | C₂H₅I | 0; 0.3 | 74 | 99(R) |
| 41 | Same as Example 38 | (t)But—O-C(=O)-CH₂Br | −20; 2 | 60 | 93(R) |
| 42 | Same as Example 38 | N-Boc-indol-3-yl-CH₂Br | −20; 2.5 | 70 | 92(R) |

NMR spectra and analytical conditions of HPLC regarding the resultant alkylated products are shown as follows.

Example 39

300 MHz $^1$H-NMR(CDCl$_3$): δ5.65–5.80(1H, m, CH=C), 5.11–5.17(2H, m, C=CH$_2$), 2.50(1H, dd, J=6.6, 13.5 Hz, CHC=C), 2.23(1H, dd, J=8.3, 13.5 Hz, CHC=C), 1.60(2H, s, NH$_2$), 1.46(9H, s, $^t$Bu), 1.29(3H, s, CH$_3$); HPLC analysis of the corresponding N-benzoate: DAICEL CHIRALCEL OD, hexane: isopropanol=100:1, flow rate=0.5 mL/min; Retention time, 17.6 min (R) and 25.9 min (S).

Example 40

300 MHz $^1$H-NMR(CDCl$_3$); δ1.66–1.79(1H, m, CHCH$_3$), 1.65(2H, br, NH$_2$), 1.48–1.60(1H, m, CHCH$_3$), 1.46(9H, s, $^t$Bu), 1.27(3H, s, CH$_3$), 0.87(3H, t, J=7.5 Hz, CH$_2$CH$_3$); HPLC analysis of the corresponding N-benzoate: DAICEL CHIRALPAK AD, hexane: isopropanol=150:1, flow rate=0.5 mL/min; Retention time, 28.1 min(R) and 31.5 min(S).

Example 41

300 MHz $^1$H-NMR(CDCl$_3$): δ2.82(1H, d, J=16.8 Hz, CHC=O), 2.44(1H, d, J=16.8 Hz, CHC=O), 1.86(2H, br s, NH$_2$), 1.45(9H, s, $^t$Bu), 1.44(9H, s, $^t$Bu), 1.26(3H, s, CH$_3$); HPLC analysis of the corresponding N-benzoate: DAICEL CHIRALCEL OD, hexane: isopropanol=100:1, flow rate=0.5 mL/min; Retention time, 14.9 min(R) and 20.6 min(S).

Example 42

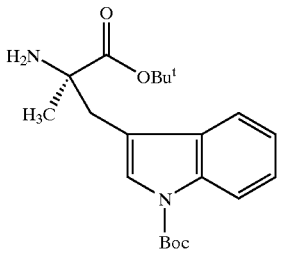

300 MHz $^1$H-NMR(CDCl$_3$): δ8.15(1H, m, Ph), 7.64(1H, m, Ph), 7.45(1H, br s, C=CH–N), 7.22–7.34(2H, m, Ph), 3.18(1H, dd, J=0.9, 14.1 Hz, CHC=C–N), 2.93(1H, dd, J=0.6, 14.1 Hz, CHC=C–N), 1.65(9H, s, $^t$Bu), 1.62(2H, s, NH$_2$), 1.46(9H, s, $^t$Bu), 1.41(3H, s, CH$_3$); HPLC analysis: DAICEL CHIRALPAK AD, hexane: isopropanol=30:1, flow rate=0.5 mL/min; Retention time, 12.2 min(R) and 17.7 min(S).

Example 43

Benzylated compounds were obtained by using compound produced in Reference Example 1 in the same manner as in Example 38 (yield 72%, optical purity 87%). Moreover, the allylattion product was also obtained in the same manner [yield, 75%; optical purity, 97% e.e.(R)]. The characteristics of those compounds are shown as follows.

benzylation product

300 MHz $^1$H-NMR(CDCl$_3$): δ7.20–7.30(5H, m, Ph), 3.12 (1H, d, J=13.1 Hz, PhCH), 2.71(1H, d, J=13.1 Hz, PhCH), 1.88(1H, dd, J=6.8, 13.7 Hz, $^i$PrCH), 1.75(1H, m, (CH$_3$)$_2$CH), 1.56(2H, br s, NH$_2$), 1.53(1H, dd, J=5.3, 13.7 Hz, $^i$PrCH), 1.44(9H, s, $^t$Bu), 0.98(3H, d, J=6.8 Hz, CH$_3$), 0.91(3H, d, J=6.8 Hz, CH$_3$); IR(film) 2957, 1724, 1603, 1497, 1456, 1393, 1367, 1236, 1153, 1128, 849, 739, 702 cm$^{-1}$. MS: m/z278([M+H]$^+$), 186(100%), 176, 91, 57, HRMS C$_{17}$H$_{27}$NO$_2$ (calculated): 278.2120([M+H]$^+$). (observed): 278.2135([M+H]$^+$). HPLC analysis: DAICEL CHIRALPAK AD, hexane: isopropanol=100:1, flow rate= 0.5 mL/min, Retention time; 13.9 min(majar enantiomer) and 15.6 min(minor enantiomer).

allylation product

300 MHz $^1$H-NMR(CDCl$_3$): δ5.61–5.75(1H, m, CH=C), 5.11–5.17(2H, m, C=CH$_2$), 2.52(1H, ddt, J=1.2, 6.3, 13.5 Hz, CHC=C), 2.16(1H, dd, J=8.6, 13.5 Hz, CHC=C), 1.68–1.79(2H, m, (CH$_3$)$_2$CH and $^i$PrCH), 1.59(2H, br s, NH$_2$), 1.44–1.54(1H, m, $^i$PrCH), 1.47(9H, s, $^t$Bu), 0.95(3H, d, J=6.5 Hz, CH$_3$), 0.88(3H, d, J=6.5 Hz, CH$_3$); IR(film) 3080, 2957, 2918, 1726, 1641, 1603, 1474, 1393, 1367, 1234, 1144, 993, 920, 853, 756, 664 cm$^{-1}$. MS: m/z228 ([M+H]$^+$)(100%), 226, 186, 170, 85, 57, 37. HRMS C$_{13}$H$_{25}$NO$_2$ (calculated): 228.1963([M+H]$^+$). (observed): 228.1948([M+H]$^+$). HPLC analysis: DAICEL CHIRALCEL OD, hexane: isopropanol=150:1, flow rate=0.5 mL/min. Retention time; 12.4 min(minor enantiomer) and 5.8 min (major enantiomer).

Example 44

In the same manner as in Example 37, dialkyl compounds were produced by using 2-methyl-2-propenyl bromide or propargyl bromide instead of benzyl bromide. The characteristics of the compounds are shown as follows.

2-methyl-2-propenyl product

300 MHz $^1$H-NMR(CDCl$_3$): δ5.64–5.78(1H, m, CH=C), 5.12–5.19(2H, m, C=CH$_2$), 4.90(1H, m, C(CH$_3$)=CH), 4.80

(1H, m, C(CH$_3$)=CH), 2.62(1H, d, J=14.0 Hz, CHC(CH$_3$)=C), 2.56(1H, ddt, J=1.2, 6.6, 13.5 Hz, CHC=C), 2.24(1H, d, J=14.0 Hz, CHC(CH$_3$)=C), 2.20(1H, dd, J=8.3, 13.5 Hz, CHC=C), 1.74(3H, s, CH$_3$C=C), 1.64(2H, s, NH$_2$), 1.43(9H, s, $^t$Bu); IR(liquid film) 3078, 2978, 2924, 1726, 1641, 1597, 1458, 1393, 1369, 1229, 1159, 1053, 993, 899, 843 cm$^{-1}$. MS: m/z226([M+H]$^+$)(100%), 184, 170, 124, 57. HRMS C$_{13}$H$_{23}$NO$_2$ (calculated): 226.1806([M+H]$^+$). (observed): 226.1795([M+H]$^+$). HPLC analysis: DAICEL CHIRALCEL OD, hexane: isopropanol=300:1, flow rate=0.5 mL/min; Retention time, 25.3 min(major enantiomer) and 35.1 min (minor enantiomer).

Propargyl product

300 MHz $^1$H-NMR(CDCl$_3$): δ5.65–5.79(1H, m, CH=C), 5.12–5.20(2H, m, C=CH$_2$), 2.64(1H, dd, J=2.7, 16.5 Hz, CHC=C), 2.52(1H, ddt, J=1.2, 6.9, 13.5 Hz, CHC=C), 2.41(1H, dd, J=2.7, 16.5 Hz, CHC=C), 2.29(1H, ddt,29(1H, ddt, J=0.9, 8.0, 13.5 Hz, CHC=C), 2.05(1H, t, J=2.7 Hz, C=CH), 1.75(2H, br s, NH$_2$), 1.48(9H, s, $^t$Bu); IR(film)3377, 3310, 3078, 2980, 2932, 1732, 1641, 1597, 1437, 1394, 1369, 1329, 1231, 1159, 1034, 997, 920, 845, 752, 646 cm$^{-1}$. MS: m/z210([M+H]$^+$)(100%), 168, 108, 57. HRMS C$_{12}$H$_{19}$NO$_2$ (calculated): 210.1494([M+H]$^+$), (observed): 210.1485([M+H]$^+$). GC analysis: GL SCIENCE CP-CHIRASIL-DEX CS, Retention time; 16.1 min(minor enantiomer) and 16.7 min(major enantiomer).

Reference Example 1

Aldimine Schiff base was prepared by reacting leucine tert-butylester as a raw material with p-chlorobenzaldehyde according to the conventional procedures. The characteristics of the Schiff base are shown as follows.

300 MHz $^1$H-NMR(CDCl$_3$); δ8.24(1H, s, CH=N), 7.73 (2H, d, J=8.7 Hz, p-Cl-Ph), 7.39(2H, d, J=8.7 Hz, p-Cl-Ph), 3.96(1H, dd, J=6.2, 8.0 Hz, CHC=O), 1.77–1.82(2H, m, $^i$PrCH$_2$), 1.56(1H, m, (CH$_3$)$_2$CH), 1.47(9H, s, $^t$Bu), 0.95 (3H, d, J=6.6 Hz, CH$_3$), 0.89(3H, d, J=6.6 Hz, CH$_3$); IR(KBr) 2980, 2959, 2934, 1736, 1641, 1597, 1573, 1491, 1466, 1393, 1366, 1339, 1275, 1209, 1146, 1088, 1063, 1015, 829, 772 cm$^{-1}$.;MS: m/z310([M+H]$^+$), 308, 210, 208, 57(100%). C$_{17}$H$_{24}$ClNO$_2$ (calculated): C, 65.90; H, 7.81; N, 4.52; Cl, 11.44. (observed); C, 65.92; H, 7.84; N, 4.55; Cl, 11.39.

Reference Example 2

Aldimine Schiff base was prepared by reacting phenylalanine tert-butylester as a raw material with p-chlorobennzaldehyde according to the conventional procedures. The characteristics of the Schiff base are shown as follows:

300 MHz $^1$H-NMR(CDCl$_3$): δ7.88(1H, s, CH=N), 7.64 (2H, d, J=8.7 Hz, p-Cl-Ph), 7.36(2H, d, J=8.7 Hz, p-Cl-Ph), 7.16–7.24(5H, m, Ph), 4.06(1H, dd, J=5.4, 8.7 Hz, CHC=O), 3.32(1H, dd, J=5.4, 13.5 Hz, PhCH), 3.10(1H, dd, J=8.7, 13.5 Hz, PhCH), 1.44(9H, s, $^t$Bu); IR(KBr) 2984, 2882, 2808, 1724, 1647, 1593, 1491, 1373, 1279, 1155, 1084, 847, 826, 760, 700 cm$^{-1}$, MS: m/z343(M$^+$)(100%), 2.78, 244, 242, 186, 91, 57, C$_{20}$H$_{22}$ClNO$_2$ (calculated): C, 69.86; H, 6.45; N, 4.07; Cl, 10.31. (observed): C, 69.89; H, 6.57; N, 4.05; Cl, 10.33.

Various other modifications will be apparent to and can be readily made by those skilled in the art without departing from the scope and spirit of the invention. Accordingly, it is not intended that the scope of claims appended hereto be limited to the description as set forth herein, but rather that the claims be broadly construed.

We claim:

1. A method for stereoselectively producing a compound of general formula (XXI):

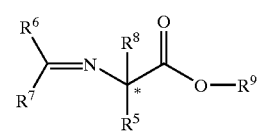

wherein

R$^5$ is alkyl group having 1 to 6 carbon atoms which may be branched or form a cyclic group; allyl or substituted allyl group having 3 to 9 carbon atoms which may be branched or form a cyclic group; aralkyl group which may be substituted with alkyl group having 1 to 4 carbon atoms, alkoxy group having 1 to 3 carbon atoms, a halogen atom, aryl group which may be substituted with alkyl group having 1 to 4 carbon atoms, alkoxy group having 1 to 3 carbon atoms or a halogen atom, or heteroaryl group which may be substituted with alkyl group having 1 to 4 carbon atoms, alkoxy group having 1 to 3 carbon atoms or a halogen atom; heteroaralkyl group which may be substituted with alkyl group having 1 to 4 carbon atoms, alkoxy group having 1 to 3 carbon atoms, a halogen atom, aryl group which may be substituted with alkyl group having 1 to 4 carbon atoms, alkoxy group having 1 to 3 carbon atoms or a halogen atom, or heteroaryl group which may be substituted with alkyl group having 1 to 4 carbon atoms, alkoxy group having 1 to 3 carbon atoms or a halogen atom; or propargyl or substituted propargyl group which having 3 to 9 carbon atoms which may be branched;

R$^6$ and R$^7$ are the same or different and are hydrogen atoms, an aryl group which may be substituted with alkyl group having 1 to 3 carbon atoms, alkoxy group having 1 to 3 carbon atoms or a halogen atom, with proviso excepting that they are hydrogen atoms simultaneously;

R$^8$ is hydrogen atom; aryl group which may be substituted with alkyl group having 1 to 3 carbon atoms, alkoxy group having 1 to 3 carbon atoms or a halogen atom; alkyl group having 1 to 6 carbon atoms which may be branched or form a cyclic group; aralkyl group which may be substituted with alkyl group having 1 to 3 carbon atoms, alkoxy group having 1 to 3 carbon atoms or a halogen atom; and R$^9$ is alkyl group having 1 to 4 carbon atoms; comprising; alkylating a compound expressed by the general formula (XIX):

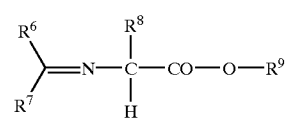

wherein R$^6$ and R$^7$ are the same or different and are hydrogen atoms, an aryl group which may be substituted with alkyl group having 1 to 3 carbon atoms, alkoxy group having 1 to 3 carbon atoms or a halogen atom, with proviso excepting that they are hydrogen atoms simultaneously; R$^8$ is hydrogen atom; aryl group which may be substituted with alkyl group having 1 to 3 carbon atoms, alkoxy group having 1 to 3 carbon atoms or a halogen atom; alkyl group having 1 to 6 carbon atoms which may be branched or form a cyclic group; aralkyl which may be substituted with alkyl group having 1 to 3 carbon atoms, alkoxy group having 1 to 3 carbon atoms or a halogen atom; and $R^9$ is alkyl group having 1 to 4 carbon atoms;

with a compound of general formula (XX):

$$R^5-W \quad (XX)$$

wherein $R^5$ is alkyl group having 1 to 6 carbon atoms which may be branched or form a cyclic group; allyl or substituted allyl group having 3 to 9 carbon atoms which may be branched or form a cyclic group; aralkyl group which may be substituted with alkyl group having 1 to 4 carbon atoms, alkoxy group having 1 to 3 carbon atoms, a halogen atom, aryl group which may be substituted with alkyl group having 1 to 4 carbon atoms, alkoxy group having 1 to 3 carbon atoms or a halogen atom, or heteroaryl group which may be substituted with alkyl group having 1 to 4 carbon atoms, alkoxy group having 1 to 3 carbon atoms or a halogen atom; heteroaralkyl group which may be substituted with alkyl group having 1 to 3 carbon atoms, alkoxy group having 1 to 3 carbon atoms, a halogen atom, aryl group which may be substituted with alkyl group having 1 to 3 carbon atoms, alkoxy group having 1 to 3 carbon atoms or a halogen atom, or heteroaryl group which may be substituted with alkyl group having 1 to 4 carbon atoms, alkoxy group having 1 to 3 carbon atoms or a halogen atom; or propargyl or substituted propargyl group which having 3 to 9 carbon atoms which may be branched; and W is a functional group having leaving ability;

using the compound of formula (I):

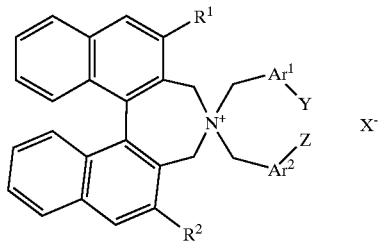

I wherein $R^1$ and $R^2$ are groups independently selected from the group consisting of a hydrogen atom; a linear alkyl group having 1 to 6 carbon atoms; a branched alkyl group having 2 to 6 carbon atoms; a cyclic alkyl group having 3 to 6 carbon atoms; a linear alkenyl group having 2 to 6 carbon atoms; a branched alkenyl group having 2 to 6 carbon atoms; a cyclic alkenyl group having 3 to 6 carbon atoms; a linear alkynyl group having 2 to 6 carbon atoms; a branched alkynyl group having 3 to 6 carbon atoms; a cyclic alkynyl group having 3 to 6 carbon atoms; an aralkyl group which may be substituted with an alkyl group having 1 to 4 carbon atoms, an alkoxy group having 1 to 3 carbon atoms or a halogen atom; a heteroaralkyl group which may be substituted with an alkyl group having 1 to 4 carbon atoms, an alkoxy group having 1 to 3 carbon atoms or a halogen atom; an aryl group which may be substituted with an alkyl group having 1 to 4 carbon atoms, an alkoxy group having 1 to 3 carbon atoms or a halogen atom; a heteroaryl group which may be substituted with an alkyl group having 1 to 4 carbon atoms, and alkoxy group having 1 to 3 carbon atoms or a halogen atom; a ($C_1$ to $C_3$ alkoxy) carbonyl group; a carbamoyl group; a N-($C_1$ to $C_4$ alkyl) carbamoyl group; and a N,N-di($C_1$ to $C_4$ alkyl) carbamoyl group (wherein alkyl may be the same or different), and $R^1$ and $R^2$ may be the same or different;

$Ar^1$ and $Ar^2$ are groups independently selected from the group consisting of an aryl group which may be substituted with an alkyl group having 1 to 4 carbon atoms, an alkoxy group having 1 to 3 carbon atoms or a halogen atom; and a heteroaryl group which may be substituted with an alkyl group having 1 to 4 carbon atoms, an alkoxy group having 1 to 3 carbon atoms or a halogen atom, and $Ar^1$ and $Ar^2$ may be the same or different;

X is a halide anion; and

Y and Z are groups independently selected from the group consisting of a hydrogen atom; a halogen atom; an alkyl group having 1 to 4 carbon atoms; and an alkoxy group having 1 to 3 carbon atoms, and Y and Z may be the same or different, or may form a single bond, which is pure regarding axial chirality, as a phase-transfer catalyst in a solvent and in the presence of an inorganic base.

2. A method according to claim 1 wherein the phase-transfer catalyst is a spiro type, and Y and Z form a single bond, and the compound is expressed by the formula (II):

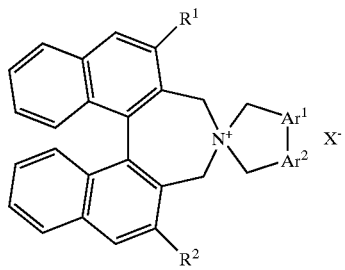

II

3. A method according to claim 2, wherein $Ar^1$ and $Ar^2$ are β-naphthyl groups and each $Ar^1$ and $Ar^2$ is bound to α-site of the other group, $X^-$ is a bromide anion, and the compound is expressed by the formula (III):

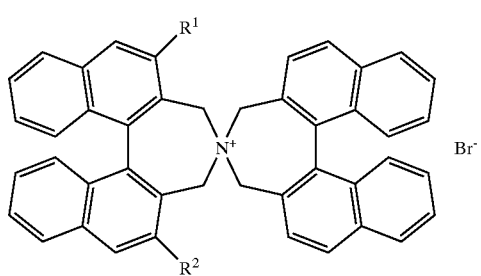

III

4. A method according to claim 3, wherein both $R^1$ and $R^2$ are phenyl, or both $R^1$ and $R^2$ are β-naphthyl.

* * * * *